(12) United States Patent
Skerra et al.

(10) Patent No.: US 8,536,307 B2
(45) Date of Patent: *Sep. 17, 2013

(54) ANTICALINS

(75) Inventors: Arne Skerra, Freising (DE); Gerald Beste, Munich (DE); Frank Schmidt, Frankfurt (DE); Thomas Stibora, Michendorf (DE)

(73) Assignee: Pieris AG, Weihenstephan (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/423,666

(22) Filed: Mar. 19, 2012

(65) Prior Publication Data
US 2012/0244596 A1 Sep. 27, 2012

Related U.S. Application Data

(63) Continuation of application No. 12/654,809, filed on Jan. 5, 2010, now Pat. No. 8,158,753, which is a continuation of application No. 11/224,071, filed on Sep. 13, 2005, now Pat. No. 7,723,476, which is a continuation of application No. 09/509,444, filed as application No. PCT/DE98/02898 on Sep. 25, 1998, now Pat. No. 7,250,297.

(30) Foreign Application Priority Data

Sep. 26, 1997 (DE) .................................. 197 42 706

(51) Int. Cl.
*A61K 38/00* (2006.01)
(52) U.S. Cl.
USPC ........................................................ 530/350
(58) Field of Classification Search
None
See application file for complete search history.

(56) References Cited

U.S. PATENT DOCUMENTS

| | | | |
|---|---|---|---|
| 6,020,163 | A | 2/2000 | Conklin |
| 6,566,073 | B1 | 5/2003 | Rivera et al. |
| 7,118,915 | B2 | 10/2006 | Vogt et al. |

FOREIGN PATENT DOCUMENTS

WO WO 96/23879 A1 8/1996

OTHER PUBLICATIONS

Wu et al., Gaodeng Xuexiao Huaxue Xuebao (2008), 29(3), 528-532; abstract only.*
Schlehuber and Skerra, Biophysical Chemistry 96 (2002) 213-228.*
Beste et al., Proc. Natl. Acad. Sci. USA, 1999; 96:1898-1903.
Flower, Darren R., "Multiple Molecular Recognition Properties of the Lipocalin Protein Family," Journal of Molecular Recognition, 1995, 8:185-195.
Flower, Darren R., "The lipocalin protein family: structure and function," Biochem. J., 1996, 318:1-14.
Gill et al., Curr. Opin. Biotechnol., 2006, 17(6):653-658.
Godovac-Zimmermann, Jasminka, "The structural motif of β-lactoglobulin and retinol-binding protein: a basic framework for binding and transport of small hydrophobic molecules?", TIBS, Feb. 1988, vol. 13, pp. 64-66.
Huber et al., "Molecular Structure of the Bilin Protein (BBP) from *Pieris brassicae* After Refinement at 2•) ÅResolution," J. Mol. Biol., 1987, 198:499-513.
Korndoerfer et al., "Crystallographic Analysis of an Anticalin" with Tailored Specificity for Fluorescein Reveals High Structural Plasticity of the Lipocalin Loop Region, Proteins: Structure, Function and Bioinformatics, 2003, vol. 53, pp. 121-129.
Korndoerfer et al., "Structural Mechanism of Specific Ligand Recognition by a Lipocalin Tailored for the Complexation of Digoxigenin," J. Mol. Biol., 2003, vol. 330, pp. 385-396.
Mercader et al., "Generagion of anticalins with specificity for a nonsymmetric phthalic acid ester," Analytical Biochemistry, 2002, vol. 308, 269-277.
Mueller et al., "Functional Expression of the Uncomplexed Serum Retinol-binding Protein in *Escherichia coli*," J. Mol. Biol., 1993, 230:725-732.
Mueller et al., "Grafting of High-Affinity Zn(II)-Binding Site on the γ-Barrel of Retinol-Binding Protein Results in Enhanced Folding Stability and Enables Simplified Purification," Biochemistry, 1994, 33:14126-14135.
Ngo et al., 1994, The Protein Folding Problem and Tertiary Structure Prediction, pp. 492-495.
Ramoni et al., J. Phys.: Condes . . . Matter, 19, 2007.
Schlehuber et al., Drug Discovery Today, 2005, 10(1):23-33.
Schmidt et al., "The bilin-binding protein of Pieris brassicae cDNA sequence and regulation of expression reveal distinct features of this insect pigment protein," Eur. J. Biochem., 1994, 219:855-863.
Sivaprasadarao et al., "Lipocalin structure and function," Biochemical Study Transactions, 1990, 619-622.
Skerra, A., FEBS J., 2008, 275:2677-2683.
Skerra, A., J. Mol. Recognit., 2000; 13:167-187.
Skerra, Arne, "Lipocalins as a scaffold," Biochim. Et. Biophys. Acta, 2000, vol. 1482, pp. 337-350.
Stump et al., "Site-directed Mutagenesis of Rat Cellular Retinol-binding Protein," J. Biol. Chem., Mar. 1991, 266(7):4622-4630.
Vogt et al., ChemBioChem 2004, 5:191-199.
Wells, 1990, Biochemistry, 29:8509-8517.

\* cited by examiner

*Primary Examiner* — Bridget E Bunner
*Assistant Examiner* — Christina Borgeest
(74) *Attorney, Agent, or Firm* — Foley & Lardner LLP

(57) ABSTRACT

The invention relates to the production of novel proteins exhibiting binding activity for certain ligands, the so-called anticalins. To this end, the structure of peptides of the lipocalin family is modified by amino acid replacement in their natural ligand binding pocket using genetic engineering methods. Like immunoglobulin, the anticalin thus obtained can be used to identify or bind molecular structures.

11 Claims, 8 Drawing Sheets

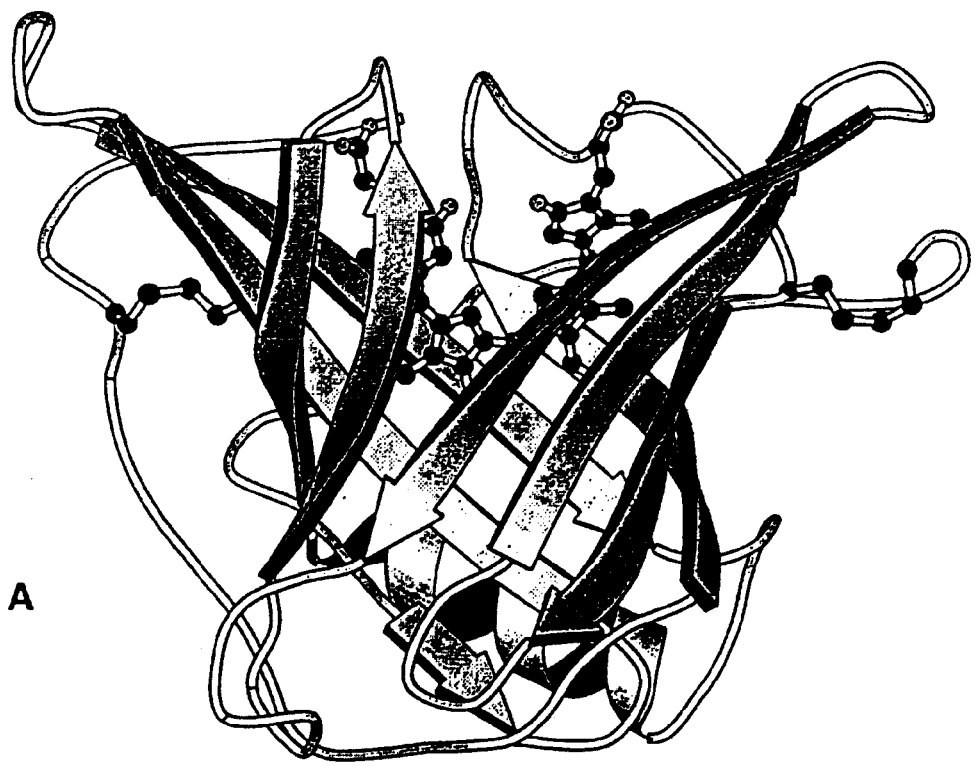
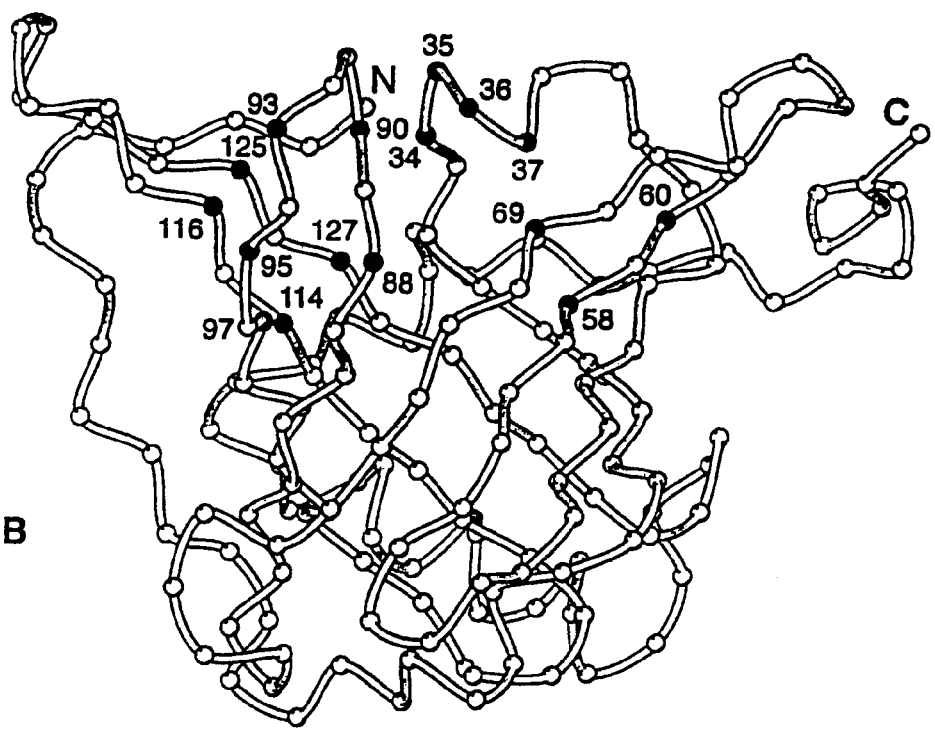
Fig. 1

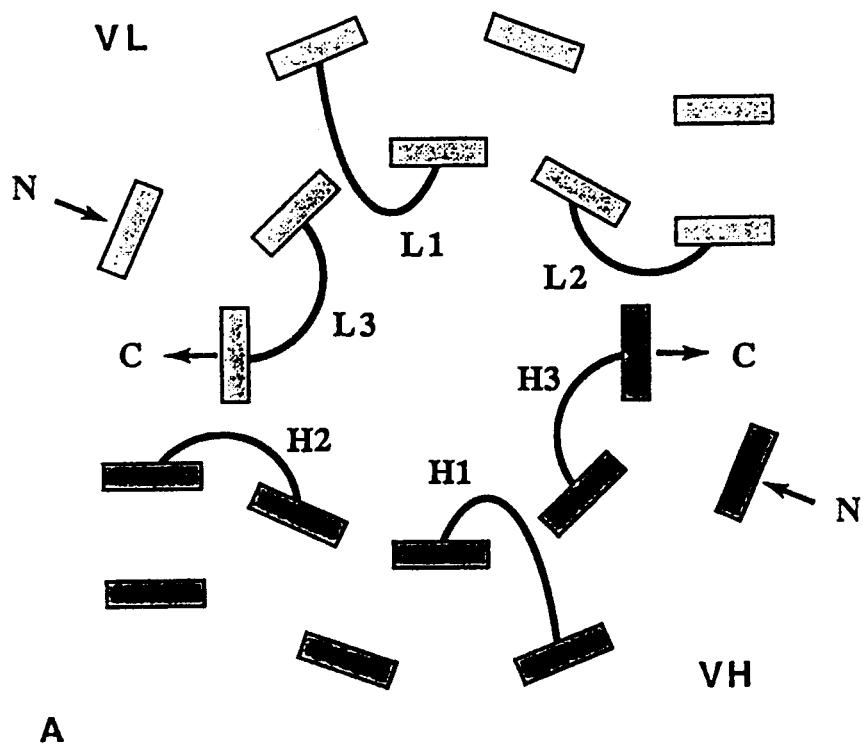
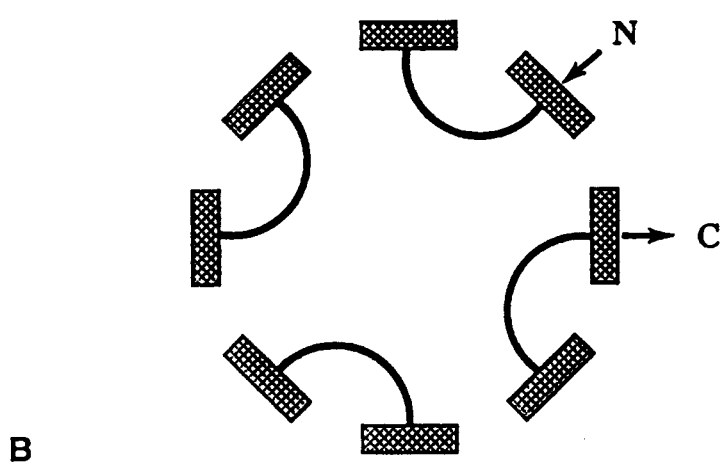
Fig. 2

```
Rbp    1    ERDCRVSSFRVKENFDKARFSGTWYAMAKKDPEGLFLQDNIVAEFSV. 47
ApoD   1    QAFHLGKCPNPPVQENFDVNKYLGRWYEIEKIPTTFEN.GRCIQANYSLM 49
Bbp    1    NVYHDGACPEVKPVDNFDWSNYHGKWWEVAKYPNSVEKYGKCGWAEYTP. 49
                                 ****
                              ================

Rbp    48   DETGQMSATAKGRVRLLNNWDVCADMVGTFTDTEDP..AKFKMKYWGVAS 95
ApoD   50   ENGKIKVLNQELRADG.....TVNQIEGEATPVNLT..EPAKLEVKFSWF 92
Bbp    50   E.GKSVKVSNYHVIHG.....KEYFIEGTAYPVGDSKIGKIYHKLTYGGV 93
                 * *                *              * *   *
              ================                    ========

Rbp    96   FLQKGNDDHWIVDTDYDTYAVQYSCRLLNLDGTCADSYSFVFSRDPNGLP 145
ApoD   93   ...MPSAPYWILATDYENYALVYSCTCI.IQ.LFHVDFAWILARNPNL.P 136
Bbp    94   ...TKENVFNVLSTDNKNYIIGYYCKYD.EDKKGHQDFVWVLSRSKVL.T 138
                  * *              * *          * *
              =========            =================

Rbp    146  PEAQKIVRQRQEEL.CLA.RQYRLIVH...NGYCDGRSERNLL 183
ApoD   137  PETVDSLKNILT.SNNIDVKKMTVTD..QVNCPKLS 169
Bbp    139  GEAKTAVENYLIGSPVVDSQKLVYSDFSEAACKVNN 174
```

Fig. 3

1. PCR (A + B)
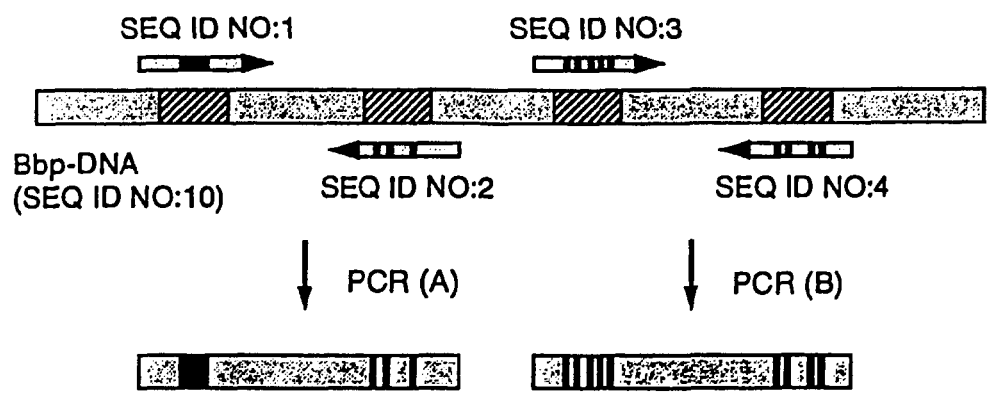
2. PCR
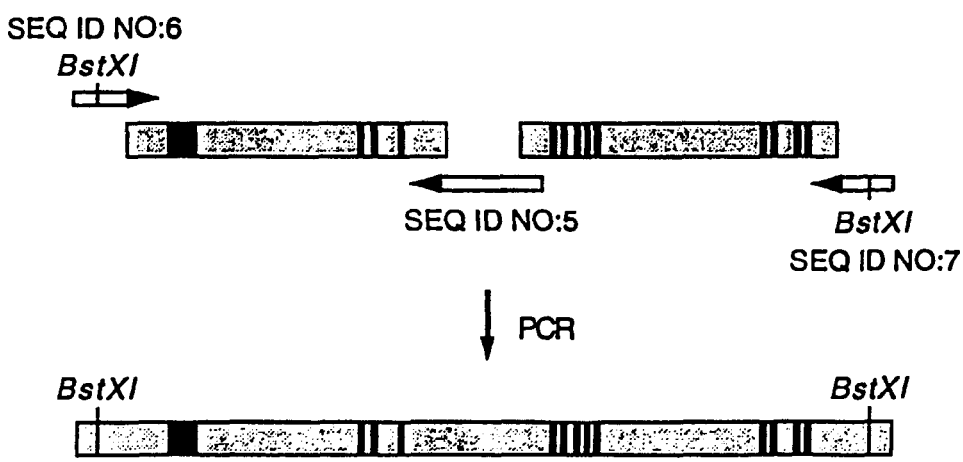
Fig. 4

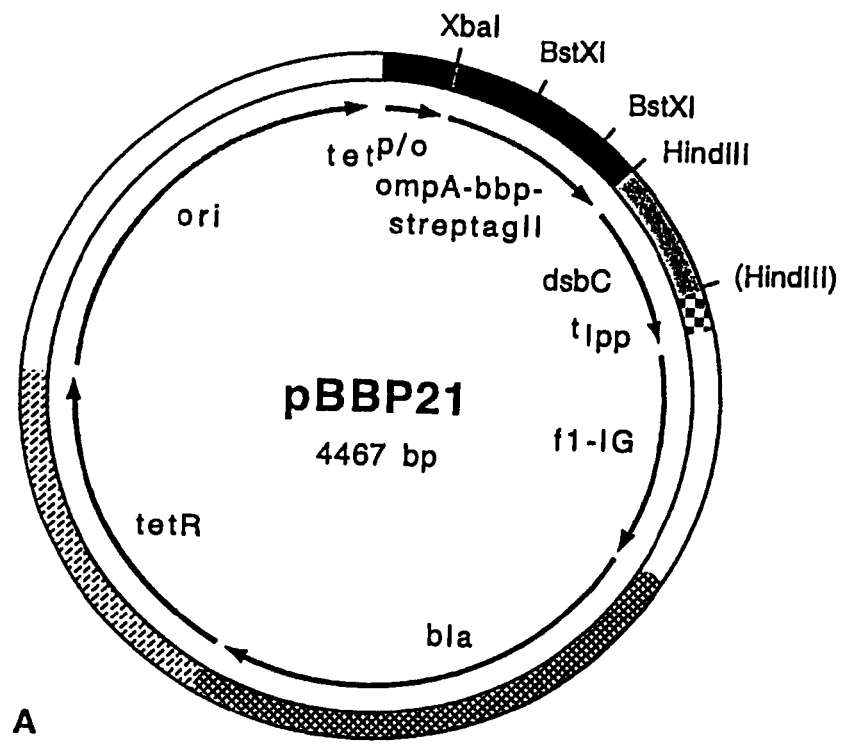
A
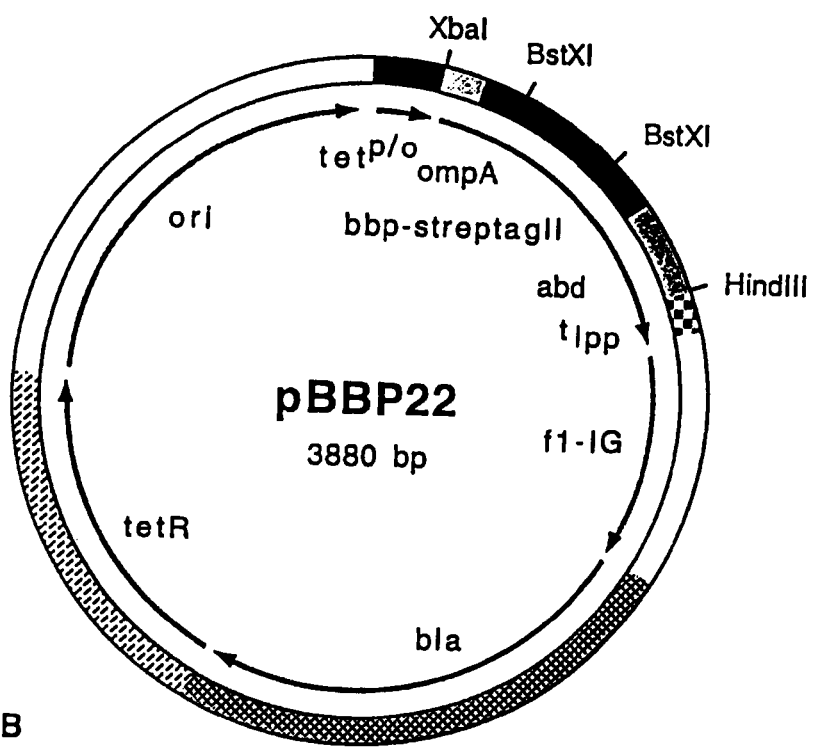
B
Fig. 6

SEQUENCE LISTING

<160> NUMBER OF SEQ ID NOS: 20

<210> SEQ ID NO 1
<211> LENGTH: 64
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<221> NAME/KEY: modified_base
<222> LOCATION: (35)..(36)
<223> OTHER INFORMATION: a, c, g or t
<220> FEATURE:
<221> NAME/KEY: modified_base
<222> LOCATION: (38)
<223> OTHER INFORMATION: a, c, g or t
<220> FEATURE:
<221> NAME/KEY: modified_base
<222> LOCATION: (41)..(42)
<223> OTHER INFORMATION: a, c, g or t
<220> FEATURE:
<221> NAME/KEY: modified_base
<222> LOCATION: (44)..(45)
<223> OTHER INFORMATION: a, c, g or t

<400> SEQUENCE: 1
ccatggtaaa tggtgggaag tcgccaaata ccccnnknms nnsnnkaagt acggaaagtg      60
cgga                                                                  64

<210> SEQ ID NO 2
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g or t
<220> FEATURE:
<221> NAME/KEY: modified_base
<222> LOCATION: (46)..(47)
<223> OTHER INFORMATION: a, c, g or t
<220> FEATURE:
<221> NAME/KEY: modified_base
<222> LOCATION: (52)..(53)
<223> OTHER INFORMATION: a, c, g or t

<400> SEQUENCE: 2
gggtaggcgg taccttcsnn aaagtattcc ttgccgtgga ttacmnngta snncgaaact      60
ttgacactct t                                                          71

<210> SEQ ID NO 3
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(28)
<223> OTHER INFORMATION: a, c, g or t
<220> FEATURE:
<221> NAME/KEY: modified_base
<222> LOCATION: (33)..(34)
<223> OTHER INFORMATION: a, c, g or t
<220> FEATURE:
<221> NAME/KEY: modified_base
<222> LOCATION: (42)..(43)
<223> OTHER INFORMATION: a, c, g or t
<220> FEATURE:
<221> NAME/KEY: modified_base
<222> LOCATION: (54)..(55)
<223> OTHER INFORMATION: a, c, g or t

<400> SEQUENCE: 3
ccaagattgg aaagatctac cacagcnnsa ctnnkggagg tnnsaccvvs gagnnkgtat      60
tcaacgtact ctcc                                                       74
```

```
<210> SEQ ID NO 4
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g or t
<220> FEATURE:
<221> NAME/KEY: modified_base
<222> LOCATION: (26)..(27)
<223> OTHER INFORMATION: a, c, g or t
<220> FEATURE:
<221> NAME/KEY: modified_base
<222> LOCATION: (53)..(54)
<223> OTHER INFORMATION: a, c, g or t
<220> FEATURE:
<221> NAME/KEY: modified_base
<222> LOCATION: (59)..(60)
<223> OTHER INFORMATION: a, c, g or t

<400> SEQUENCE: 4
tctggagagc acccagacmn ngtcsnngtg tcccttcttg tcctcgtcgt asnngcamnn        60
gtatccgatg atgtagtt                                                     78

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agatctttcc aatcttggag tcaccaactg ggtaggcggt accttc                      46

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cttcgactgg tcccagtacc atggtaaatg gtggga                                 36

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caccagtaag gaccatgctt ctggagagca cccagac                                37

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 8
gacggtgcct gtcccga                                                    17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gactactggg gagccga                                                    17

<210> SEQ ID NO 10
<211> LENGTH: 1219
<212> TYPE: DNA
<213> ORGANISM: Artificial Sequence
<220> FEATURE:
<223> OTHER INFORMATION: Description of Artificial Sequence: Fragment of
      plasmid pBBP20 encoding fusion protein made of
      bilin-binding protein, Strep-Tag II and fragment
      of phage coat protein
<220> FEATURE:
<221> NAME/KEY: sig_peptide
<222> LOCATION: (22)..(84)
<220> FEATURE:
<221> NAME/KEY: mat_peptide
<222> LOCATION: (85)..(1209)
<220> FEATURE:
<221> NAME/KEY: CDS
<222> LOCATION: (22)..(1209)
<220> FEATURE:
<221> NAME/KEY: misc_feature
<222> LOCATION: (85)..(606)
<223> OTHER INFORMATION: Mature bilin-binding protein
<220> FEATURE:
<221> NAME/KEY: misc_feature
<222> LOCATION: (607)..(636)
<223> OTHER INFORMATION: Strep-Tag II-affinity tag
<220> FEATURE:
<221> NAME/KEY: misc_feature
<222> LOCATION: (637)..(639)
<223> OTHER INFORMATION: Amber stop codon
<220> FEATURE:
<221> NAME/KEY: misc_feature
<222> LOCATION: (640)..(1209)
<223> OTHER INFORMATION: Amino acids 217-406 of the coat protein pIII

<400> SEQUENCE: 10
tctagttaac gagggcaaaa a atg aaa aag aca gct atc gcg att gca gtg        51
                       Met Lys Lys Thr Ala Ile Ala Ile Ala Val
                           -20                 -15 gca ctg gct ggt ttc gct acc gta gcg cag gcc gac gtg tac cac gac        99
Ala Leu Ala Gly Phe Ala Thr Val Ala Gln Ala Asp Val Tyr His Asp
    -10                 -5              -1   1                 5 ggt gcc tgt ccc gaa gtc aag cca gtc gac aac ttc gac tgg tcc cag       147
Gly Ala Cys Pro Glu Val Lys Pro Val Asp Asn Phe Asp Trp Ser Gln
             10                  15                  20 tac cat ggt aaa tgg tgg gaa gtc gcc aaa tac ccc aac tca gtt gag       195
Tyr His Gly Lys Trp Trp Glu Val Ala Lys Tyr Pro Asn Ser Val Glu
         25                  30                  35 aag tac gga aag tgc gga tgg gct gag tac act cct gaa ggc aag agt       243
Lys Tyr Gly Lys Cys Gly Trp Ala Glu Tyr Thr Pro Glu Gly Lys Ser
     40                  45                  50 gtc aaa gtt tcg aac tac cac gta atc cac ggc aag gaa tac ttt att       291
Val Lys Val Ser Asn Tyr His Val Ile His Gly Lys Glu Tyr Phe Ile
 55                  60                  65 gaa gga act gcc tac cca gtt ggt gac tcc aag att gga aag atc tac       339
Glu Gly Thr Ala Tyr Pro Val Gly Asp Ser Lys Ile Gly Lys Ile Tyr
```

-continued

| | | |
|---|---|---|
| Glu Gly Thr Ala Tyr Pro Val Gly Asp Ser Lys Ile Gly Lys Ile Tyr<br>70                             75                      80                         85 | | |
| cac agc ctg act tac gga ggt gtc acc aag gag aac gta ttc aac gta<br>His Ser Leu Thr Tyr Gly Gly Val Thr Lys Glu Asn Val Phe Asn Val<br>                        90                        95                         100 | | 387 |
| ctc tcc act gac aac aag aac tac atc atc gga tac tac tgc aaa tac<br>Leu Ser Thr Asp Asn Lys Asn Tyr Ile Ile Gly Tyr Tyr Cys Lys Tyr<br>                    105                   110                   115 | | 435 |
| gac gag gac aag aag gga cac caa gac ttc gtc tgg gtg ctc tcc aga<br>Asp Glu Asp Lys Lys Gly His Gln Asp Phe Val Trp Val Leu Ser Arg<br>           120                   125                   130 | | 483 |
| agc atg gtc ctt act ggt gaa gcc aag acc gct gtc gag aac tac ctt<br>Ser Met Val Leu Thr Gly Glu Ala Lys Thr Ala Val Glu Asn Tyr Leu<br>135                         140                   145 | | 531 |
| atc ggc tcc cca gta gtc gac tcc cag aaa ctg gta tac agt gac ttc<br>Ile Gly Ser Pro Val Val Asp Ser Gln Lys Leu Val Tyr Ser Asp Phe<br>150                         155                   160                   165 | | 579 |
| tct gaa gcc gcc tgc aag gtc aac aat agc aac tgg tct cac ccg cag<br>Ser Glu Ala Ala Cys Lys Val Asn Asn Ser Asn Trp Ser His Pro Gln<br>           170                   175                   180 | | 627 |
| ttc gaa aaa tag gct ggc ggc tct ggt ggt ggt tct ggc ggc ggc<br>Phe Glu Lys Gln Ala Gly Gly Ser Gly Gly Gly Ser Gly Gly Gly<br>        185                   190                   195 | | 675 |
| tct gag ggt ggt ggc tct gag ggt ggc ggt tct gag ggt ggc ggc tct<br>Ser Glu Gly Gly Gly Ser Glu Gly Gly Gly Ser Glu Gly Gly Gly Ser<br>           200                   205                   210 | | 723 |
| gag gga ggc ggt tcc ggt ggt ggc tct ggt tcc ggt gat ttt gat tat<br>Glu Gly Gly Gly Ser Gly Gly Gly Ser Gly Ser Gly Asp Phe Asp Tyr<br>215                         220                   225 | | 771 |
| gaa aag atg gca aac gct aat aag ggg gct atg acc gaa aat gcc gat<br>Glu Lys Met Ala Asn Ala Asn Lys Gly Ala Met Thr Glu Asn Ala Asp<br>230                         235                   240                   245 | | 819 |
| gaa aac gcg cta cag tct gac gct aaa ggc aaa ctt gat tct gtc gct<br>Glu Asn Ala Leu Gln Ser Asp Ala Lys Gly Lys Leu Asp Ser Val Ala<br>           250                   255                   260 | | 867 |
| act gat tac ggt gct gct atc gat ggt ttc att ggt gac gtt tcc ggc<br>Thr Asp Tyr Gly Ala Ala Ile Asp Gly Phe Ile Gly Asp Val Ser Gly<br>                265                   270                   275 | | 915 |
| ctt gct aat ggt aat ggt gct act ggt gat ttt gct ggc tct aat tcc<br>Leu Ala Asn Gly Asn Gly Ala Thr Gly Asp Phe Ala Gly Ser Asn Ser<br>           280                   285                   290 | | 963 |
| caa atg gct caa gtc ggt gac ggt gat aat tca cct tta atg aat aat<br>Gln Met Ala Gln Val Gly Asp Gly Asp Asn Ser Pro Leu Met Asn Asn<br>295                         300                   305 | | 1011 |
| ttc cgt caa tat tta cct tcc ctc cct caa tcg gtt gaa tgt cgc cct<br>Phe Arg Gln Tyr Leu Pro Ser Leu Pro Gln Ser Val Glu Cys Arg Pro<br>310                         315                   320                   325 | | 1059 |
| ttt gtc ttt ggc gct ggt aaa cca tat gaa ttt tct att gat tgt gac<br>Phe Val Phe Gly Ala Gly Lys Pro Tyr Glu Phe Ser Ile Asp Cys Asp<br>                330                   335                   340 | | 1107 |
| aaa ata aac tta ttc cgt ggt gtc ttt gcg ttt ctt tta tat gtt gcc<br>Lys Ile Asn Leu Phe Arg Gly Val Phe Ala Phe Leu Leu Tyr Val Ala<br>                        345                   350                   355 | | 1155 |
| acc ttt atg tat gta ttt tct acg ttt gct aac ata ctg cgt aat aag<br>Thr Phe Met Tyr Val Phe Ser Thr Phe Ala Asn Ile Leu Arg Asn Lys<br>           360                   365                   370 | | 1203 |
| gag tct taataagctt<br>Glu Ser<br>375 | | 1219 |

```
<210> SEQ ID NO 11
<211> LENGTH: 1380
<212> TYPE: DNA
<213> ORGANISM: Artificial Sequence
<220> FEATURE:
<223> OTHER INFORMATION: Description of Artificial Sequence: Fragment of
      plasmid pBBP21
<220> FEATURE:
<221> NAME/KEY: sig_peptide
<222> LOCATION: (22)..(84)
<220> FEATURE:
<221> NAME/KEY: mat_peptide
<222> LOCATION: (85)..(636)
<223> OTHER INFORMATION: Fusion protein made of bilin-binding protein
      and Strep-Tag II
<220> FEATURE:
<221> NAME/KEY: CDS
<222> LOCATION: (22)..(636)
<220> FEATURE:
<221> NAME/KEY: sig_peptide
<222> LOCATION: (658)..(717)
<220> FEATURE:
<221> NAME/KEY: mat_peptide
<222> LOCATION: (718)..(1365)
<223> OTHER INFORMATION: DsbC protein
<220> FEATURE:
<221> NAME/KEY: CDS
<222> LOCATION: (658)..(1365)
```

<400> SEQUENCE: 11

```
tctagataac gagggcaaaa a atg aaa aag aca gct atc gcg att gca gtg        51
                        Met Lys Lys Thr Ala Ile Ala Ile Ala Val
                            -20                 -15 gca ctg gct ggt ttc gct acc gta gcg cag gcc gac gtg tac cac gac        99
Ala Leu Ala Gly Phe Ala Thr Val Ala Gln Ala Asp Val Tyr His Asp
    -10                 -5              -1   1               5 ggt gcc tgt ccc gaa gtc aag cca gtc gac aac ttc gac tgg tcc cag       147
Gly Ala Cys Pro Glu Val Lys Pro Val Asp Asn Phe Asp Trp Ser Gln
                10                  15                  20 tac cat ggt aaa tgg tgg gaa gtc gcc aaa tac ccc aac tca gtt gag       195
Tyr His Gly Lys Trp Trp Glu Val Ala Lys Tyr Pro Asn Ser Val Glu
            25                  30                  35 aag tac gga aag tgc gga tgg gct gag tac act cct gaa ggc aag agt       243
Lys Tyr Gly Lys Cys Gly Trp Ala Glu Tyr Thr Pro Glu Gly Lys Ser
        40                  45                  50 gtc aaa gtt tcg aac tac cac gta atc cac ggc aag gaa tac ttt att       291
Val Lys Val Ser Asn Tyr His Val Ile His Gly Lys Glu Tyr Phe Ile
    55                  60                  65 gaa gga act gcc tac cca gtt ggt gac tcc aag att gga aag atc tac       339
Glu Gly Thr Ala Tyr Pro Val Gly Asp Ser Lys Ile Gly Lys Ile Tyr
70                  75                  80                  85 cac agc ctg act tac gga ggt gtc acc aag gag aac gta ttc aac gta       387
His Ser Leu Thr Tyr Gly Gly Val Thr Lys Glu Asn Val Phe Asn Val
                90                  95                  100 ctc tcc act gac aac aag aac tac atc atc gga tac tac tgc aaa tac       435
Leu Ser Thr Asp Asn Lys Asn Tyr Ile Ile Gly Tyr Tyr Cys Lys Tyr
            105                 110                 115 gac gag gac aag aag gga cac caa gac ttc gtc tgg gtg ctc tcc aga       483
Asp Glu Asp Lys Lys Gly His Gln Asp Phe Val Trp Val Leu Ser Arg
        120                 125                 130 agc atg gtc ctt act ggt gaa gcc aag acc gct gtc gag aac tac ctt       531
Ser Met Val Leu Thr Gly Glu Ala Lys Thr Ala Val Glu Asn Tyr Leu
    135                 140                 145 atc ggc tcc cca gta gtc gac tcc cag aaa ctg gta tac agt gac ttc       579
Ile Gly Ser Pro Val Val Asp Ser Gln Lys Leu Val Tyr Ser Asp Phe
150                 155                 160                 165 tct gaa gcc gcc tgc aag gtc aac aat agc aac tgg tct cac ccg cag       627
Ser Glu Ala Ala Cys Lys Val Asn Asn Ser Asn Trp Ser His Pro Gln
```

```
                Ser Glu Ala Ala Cys Lys Val Asn Asn Ser Asn Trp Ser His Pro Gln
                                170                 175                 180 ttc gaa aaa taataagctt cgggaagatt t atg aag aaa ggt ttt atg ttg                  678
Phe Glu Lys                          Met Lys Lys Gly Phe Met Leu
                                     -20             -15 ttt act ttg tta gcg gcg ttt tca ggc ttt gct cag gct gat gac gcg                   726
Phe Thr Leu Leu Ala Ala Phe Ser Gly Phe Ala Gln Ala Asp Asp Ala
            -10             -5              -1   1 gca att caa caa acg tta gcc aaa atg ggc atc aaa agc agc gat att                   774
Ala Ile Gln Gln Thr Leu Ala Lys Met Gly Ile Lys Ser Ser Asp Ile
        5               10              15 cag ccc gcg cct gta gct ggc atg aag aca gtt ctg act aac agc ggc                   822
Gln Pro Ala Pro Val Ala Gly Met Lys Thr Val Leu Thr Asn Ser Gly
 20              25              30              35 gtg ttg tac atc acc gat gat ggt aaa cat atc att cag ggg cca atg                   870
Val Leu Tyr Ile Thr Asp Asp Gly Lys His Ile Ile Gln Gly Pro Met
                40              45              50 tat gac gtt agt ggc acg gct ccg gtc aat gtc acc aat aag atg ctg                   918
Tyr Asp Val Ser Gly Thr Ala Pro Val Asn Val Thr Asn Lys Met Leu
            55              60              65 tta aag cag ttg aat gcg ctt gaa aaa gag atg atc gtt tat aaa gcg                   966
Leu Lys Gln Leu Asn Ala Leu Glu Lys Glu Met Ile Val Tyr Lys Ala
        70              75              80 ccg cag gaa aaa cac gtc atc acc gtg ttt act gat att acc tgt ggt                  1014
Pro Gln Glu Lys His Val Ile Thr Val Phe Thr Asp Ile Thr Cys Gly
 85              90              95 tac tgc cac aaa ctg cat gag caa atg gca gac tac aac gcg ctg ggg                  1062
Tyr Cys His Lys Leu His Glu Gln Met Ala Asp Tyr Asn Ala Leu Gly
100             105             110             115 atc acc gtg cgt tat ctt gct ttc ccg cgc cag ggg ctg gac agc gat                  1110
Ile Thr Val Arg Tyr Leu Ala Phe Pro Arg Gln Gly Leu Asp Ser Asp
            120             125             130 gca gag aaa gaa atg aaa gct atc tgg tgt gcg aaa gat aaa aac aaa                  1158
Ala Glu Lys Glu Met Lys Ala Ile Trp Cys Ala Lys Asp Lys Asn Lys
        135             140             145 gcg ttt gat gat gtg atg gca ggt aaa agc gtc gca cca gcc agt tgc                  1206
Ala Phe Asp Asp Val Met Ala Gly Lys Ser Val Ala Pro Ala Ser Cys
150             155             160 gac gtg gat att gcc gac cat tac gca ctt ggc gtc cag ctt ggc gtt                  1254
Asp Val Asp Ile Ala Asp His Tyr Ala Leu Gly Val Gln Leu Gly Val
165             170             175 agc ggt act ccg gca gtt gtg ctg agc aat ggc aca ctt gtt ccg ggt                  1302
Ser Gly Thr Pro Ala Val Val Leu Ser Asn Gly Thr Leu Val Pro Gly
180             185             190             195 tac cag ccg ccg aaa gag atg aaa gaa ttc ctc gac gaa cac caa aaa                  1350
Tyr Gln Pro Pro Lys Glu Met Lys Glu Phe Leu Asp Glu His Gln Lys
            200             205             210 atg acc agc ggt aaa taattcgcgt agctt                                              1380
Met Thr Ser Gly Lys
            215

<210> SEQ ID NO 12
<211> LENGTH: 793
<212> TYPE: DNA
<213> ORGANISM: Artificial Sequence
<220> FEATURE:
<223> OTHER INFORMATION: Description of Artificial Sequence: Fragment of
      plasmid pBBP22
<220> FEATURE:
<221> NAME/KEY: sig_peptide
<222> LOCATION: (22)..(84)
<220> FEATURE:
<221> NAME/KEY: mat_peptide
```

<222> LOCATION: (85)..(783)
<223> OTHER INFORMATION: Fusion protein made of bilin-binding protein,
      Strep-Tag II and Albumin Binding domain
<220> FEATURE:
<221> NAME/KEY: CDS
<222> LOCATION: (22)..(783)
<220> FEATURE:
<221> NAME/KEY: misc_feature
<222> LOCATION: (85)..(606)
<223> OTHER INFORMATION: Mature bilin-binding protein
<220> FEATURE:
<221> NAME/KEY: misc_feature
<222> LOCATION: (607)..(636)
<223> OTHER INFORMATION: Strep-Tag II-affinity tag
<220> FEATURE:
<221> NAME/KEY: misc_feature
<222> LOCATION: (637)..(783)
<223> OTHER INFORMATION: Albumin-Binding domain of Protein G

<400> SEQUENCE: 12

```
tctagataac gagggcaaaa a atg aaa aag aca gct atc gcg att gca gtg            51
                        Met Lys Lys Thr Ala Ile Ala Ile Ala Val
                            -20                  -15 gca ctg gct ggt ttc gct acc gta gcg cag gcc gac gtg tac cac gac            99
Ala Leu Ala Gly Phe Ala Thr Val Ala Gln Ala Asp Val Tyr His Asp
    -10              -5                  -1   1                 5 ggt gcc tgt ccc gaa gtc aag cca gtc gac aac ttc gac tgg tcc cag           147
Gly Ala Cys Pro Glu Val Lys Pro Val Asp Asn Phe Asp Trp Ser Gln
             10                  15                  20 tac cat ggt aaa tgg tgg gaa gtc gcc aaa tac ccc aac tca gtt gag           195
Tyr His Gly Lys Trp Trp Glu Val Ala Lys Tyr Pro Asn Ser Val Glu
         25                  30                  35 aag tac gga aag tgc gga tgg gct gag tac act cct gaa ggc aag agt           243
Lys Tyr Gly Lys Cys Gly Trp Ala Glu Tyr Thr Pro Glu Gly Lys Ser
     40                  45                  50 gtc aaa gtt tcg aac tac cac gta atc cac ggc aag gaa tac ttt att           291
Val Lys Val Ser Asn Tyr His Val Ile His Gly Lys Glu Tyr Phe Ile
 55                  60                  65 gaa gga act gcc tac cca gtt ggt gac tcc aag att gga aag atc tac           339
Glu Gly Thr Ala Tyr Pro Val Gly Asp Ser Lys Ile Gly Lys Ile Tyr
 70                  75                  80                  85 cac agc ctg act tac gga ggt gtc acc aag gag aac gta ttc aac gta           387
His Ser Leu Thr Tyr Gly Gly Val Thr Lys Glu Asn Val Phe Asn Val
             90                  95                 100 ctc tcc act gac aac aag aac tac atc atc gga tac tac tgc aaa tac           435
Leu Ser Thr Asp Asn Lys Asn Tyr Ile Ile Gly Tyr Tyr Cys Lys Tyr
         105                 110                 115 gac gag gac aag aag gga cac caa gac ttc gtc tgg gtg ctc tcc aga           483
Asp Glu Asp Lys Lys Gly His Gln Asp Phe Val Trp Val Leu Ser Arg
     120                 125                 130 agc atg gtc ctt act ggt gaa gcc aag acc gct gtc gag aac tac ctt           531
Ser Met Val Leu Thr Gly Glu Ala Lys Thr Ala Val Glu Asn Tyr Leu
 135                 140                 145 atc ggc tcc cca gta gtc gac tcc cag aaa ctg gta tac agt gac ttc           579
Ile Gly Ser Pro Val Val Asp Ser Gln Lys Leu Val Tyr Ser Asp Phe
150                 155                 160                 165 tct gaa gcc gcc tgc aag gtc aac aat agc aac tgg tct cac ccg cag           627
Ser Glu Ala Ala Cys Lys Val Asn Asn Ser Asn Trp Ser His Pro Gln
             170                 175                 180 ttc gaa aaa cca gct agc ctg gct gaa gct aaa gtt ctg gct aac cgt           675
Phe Glu Lys Pro Ala Ser Leu Ala Glu Ala Lys Val Leu Ala Asn Arg
         185                 190                 195 gaa ctg gac aaa tac ggt gtt tcc gac tac tac aaa aac ctc atc aac           723
Glu Leu Asp Lys Tyr Gly Val Ser Asp Tyr Tyr Lys Asn Leu Ile Asn
     200                 205                 210
```

```
aac gct aaa acc gtt gaa ggt gtt aaa gct ctg atc gac gaa att ctc    771
Asn Ala Lys Thr Val Glu Gly Val Lys Ala Leu Ile Asp Glu Ile Leu
    215                 220                 225 gca gca ctg ccg taataagctt                                         793
Ala Ala Leu Pro
230

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Biotinamidocaproyl
<220> FEATURE:
<223> OTHER INFORMATION: C-term amidated

<400> SEQUENCE: 13

Xaa Ser Pro Thr His Tyr Val
  1               5

<210> SEQ ID NO 14
<211> LENGTH: 396
<212> TYPE: PRT
<213> ORGANISM: Artificial Sequence
<220> FEATURE:
<223> OTHER INFORMATION: Description of Artificial Sequence: Fusion
      protein made of bilin-binding protein, Strep-Tag II and fragment
      of phage coat protein encoded by fragment of plasmid pBBP20

<400> SEQUENCE: 14

Met Lys Lys Thr Ala Ile Ala Ile Ala Val Ala Leu Ala Gly Phe Ala
 -20                 -15                 -10

Thr Val Ala Gln Ala Asp Val Tyr His Asp Gly Ala Cys Pro Glu Val
 -5              -1   1               5                  10

Lys Pro Val Asp Asn Phe Asp Trp Ser Gln Tyr His Gly Lys Trp Trp
                 15                  20                  25

Glu Val Ala Lys Tyr Pro Asn Ser Val Glu Lys Tyr Gly Lys Cys Gly
             30                  35                  40

Trp Ala Glu Tyr Thr Pro Glu Gly Lys Ser Val Lys Val Ser Asn Tyr
     45                  50                  55

His Val Ile His Gly Lys Glu Tyr Phe Ile Glu Gly Thr Ala Tyr Pro
 60                  65                  70                  75

Val Gly Asp Ser Lys Ile Gly Lys Ile Tyr His Ser Leu Thr Tyr Gly
                 80                  85                  90

Gly Val Thr Lys Glu Asn Val Phe Asn Val Leu Ser Thr Asp Asn Lys
             95                 100                 105

Asn Tyr Ile Ile Gly Tyr Tyr Cys Lys Tyr Asp Glu Asp Lys Lys Gly
         110                 115                 120

His Gln Asp Phe Val Trp Val Leu Ser Arg Ser Met Val Leu Thr Gly
     125                 130                 135

Glu Ala Lys Thr Ala Val Glu Asn Tyr Leu Ile Gly Ser Pro Val Val
140                 145                 150                 155

Asp Ser Gln Lys Leu Val Tyr Ser Asp Phe Ser Glu Ala Ala Cys Lys
                 160                 165                 170

Val Asn Asn Ser Asn Trp Ser His Pro Gln Phe Glu Lys Gln Ala Gly
             175                 180                 185
```

```
Gly Gly Ser Gly Gly Ser Gly Gly Ser Glu Gly Gly Ser
        190             195             200

Glu Gly Gly Ser Glu Gly Gly Ser Glu Gly Gly Ser Gly
205             210             215

Gly Gly Ser Gly Ser Gly Asp Phe Asp Tyr Glu Lys Met Ala Asn Ala
220             225             230             235

Asn Lys Gly Ala Met Thr Glu Asn Ala Asp Glu Asn Ala Leu Gln Ser
            240             245             250

Asp Ala Lys Gly Lys Leu Asp Ser Val Ala Thr Asp Tyr Gly Ala Ala
            255             260             265

Ile Asp Gly Phe Ile Gly Asp Val Ser Gly Leu Ala Asn Gly Asn Gly
            270             275             280

Ala Thr Gly Asp Phe Ala Gly Ser Asn Ser Gln Met Ala Gln Val Gly
285             290             295

Asp Gly Asp Asn Ser Pro Leu Met Asn Asn Phe Arg Gln Tyr Leu Pro
300             305             310             315

Ser Leu Pro Gln Ser Val Glu Cys Arg Pro Phe Val Phe Gly Ala Gly
            320             325             330

Lys Pro Tyr Glu Phe Ser Ile Asp Cys Asp Lys Ile Asn Leu Phe Arg
            335             340             345

Gly Val Phe Ala Phe Leu Leu Tyr Val Ala Thr Phe Met Tyr Val Phe
            350             355             360

Ser Thr Phe Ala Asn Ile Leu Arg Asn Lys Glu Ser
            365             370             375

<210> SEQ ID NO 15
<211> LENGTH: 205
<212> TYPE: PRT
<213> ORGANISM: Artificial Sequence
<220> FEATURE:
<223> OTHER INFORMATION: Description of Artificial Sequence: Fusion
      protein encoded by fragment of plasmid pBBP21

<400> SEQUENCE: 15

Met Lys Lys Thr Ala Ile Ala Ile Ala Val Ala Leu Ala Gly Phe Ala
        -20             -15             -10

Thr Val Ala Gln Ala Asp Val Tyr His Asp Gly Ala Cys Pro Glu Val
-5               -1   1              5              10

Lys Pro Val Asp Asn Phe Asp Trp Ser Gln Tyr His Gly Lys Trp Trp
                15              20              25

Glu Val Ala Lys Tyr Pro Asn Ser Val Glu Lys Tyr Gly Lys Cys Gly
            30              35              40

Trp Ala Glu Tyr Thr Pro Glu Gly Lys Ser Val Lys Val Ser Asn Tyr
        45              50              55

His Val Ile His Gly Lys Glu Tyr Phe Ile Glu Gly Thr Ala Tyr Pro
60              65              70              75

Val Gly Asp Ser Lys Ile Gly Lys Ile Tyr His Ser Leu Thr Tyr Gly
                80              85              90

Gly Val Thr Lys Glu Asn Val Phe Asn Val Leu Ser Thr Asp Asn Lys
            95              100             105

Asn Tyr Ile Ile Gly Tyr Tyr Cys Lys Tyr Asp Glu Asp Lys Lys Gly
        110             115             120

His Gln Asp Phe Val Trp Val Leu Ser Arg Ser Met Val Leu Thr Gly
    125             130             135

Glu Ala Lys Thr Ala Val Glu Asn Tyr Leu Ile Gly Ser Pro Val Val
140             145             150             155
```

```
Asp Ser Gln Lys Leu Val Tyr Ser Asp Phe Ser Glu Ala Ala Cys Lys
            160                 165                 170

Val Asn Asn Ser Asn Trp Ser His Pro Gln Phe Glu Lys
            175                 180
```

<210> SEQ ID NO 16
<211> LENGTH: 236
<212> TYPE: PRT
<213> ORGANISM: Artificial Sequence
<220> FEATURE:
<223> OTHER INFORMATION: Description of Artificial Sequence: Fusion
      protein encoded by plasmid pBBP21

<400> SEQUENCE: 16

```
Met Lys Lys Gly Phe Met Leu Phe Thr Leu Leu Ala Ala Phe Ser Gly
-20                 -15                 -10                  -5

Phe Ala Gln Ala Asp Asp Ala Ala Ile Gln Gln Thr Leu Ala Lys Met
                 -1   1               5                  10

Gly Ile Lys Ser Ser Asp Ile Gln Pro Ala Pro Val Ala Gly Met Lys
            15                  20                  25

Thr Val Leu Thr Asn Ser Gly Val Leu Tyr Ile Thr Asp Asp Gly Lys
        30                  35                  40

His Ile Ile Gln Gly Pro Met Tyr Asp Val Ser Gly Thr Ala Pro Val
    45                  50                  55                  60

Asn Val Thr Asn Lys Met Leu Leu Lys Gln Leu Asn Ala Leu Glu Lys
                    65                  70                  75

Glu Met Ile Val Tyr Lys Ala Pro Gln Glu Lys His Val Ile Thr Val
                80                  85                  90

Phe Thr Asp Ile Thr Cys Gly Tyr Cys His Lys Leu His Glu Gln Met
            95                  100                 105

Ala Asp Tyr Asn Ala Leu Gly Ile Thr Val Arg Tyr Leu Ala Phe Pro
        110                 115                 120

Arg Gln Gly Leu Asp Ser Asp Ala Glu Lys Glu Met Lys Ala Ile Trp
125                 130                 135                 140

Cys Ala Lys Asp Lys Asn Lys Ala Phe Asp Asp Val Met Ala Gly Lys
                145                 150                 155

Ser Val Ala Pro Ala Ser Cys Asp Val Asp Ile Ala Asp His Tyr Ala
            160                 165                 170

Leu Gly Val Gln Leu Gly Val Ser Gly Thr Pro Ala Val Val Leu Ser
        175                 180                 185

Asn Gly Thr Leu Val Pro Gly Tyr Gln Pro Pro Lys Glu Met Lys Glu
    190                 195                 200

Phe Leu Asp Glu His Gln Lys Met Thr Ser Gly Lys
205                 210                 215
```

<210> SEQ ID NO 17
<211> LENGTH: 254
<212> TYPE: PRT
<213> ORGANISM: Artificial Sequence
<220> FEATURE:
<223> OTHER INFORMATION: Description of Artificial Sequence: Fusion
      protein encoded by plasmid pBBP22

<400> SEQUENCE: 17

```
Met Lys Lys Thr Ala Ile Ala Ile Ala Val Ala Leu Ala Gly Phe Ala
    -20                 -15                 -10

Thr Val Ala Gln Ala Asp Val Tyr His Asp Gly Ala Cys Pro Glu Val
-5                  -1   1               5                  10

Lys Pro Val Asp Asn Phe Asp Trp Ser Gln Tyr His Gly Lys Trp Trp
```

```
                15                  20                  25
Glu Val Ala Lys Tyr Pro Asn Ser Val Glu Lys Tyr Gly Lys Cys Gly
             30                  35                  40

Trp Ala Glu Tyr Thr Pro Glu Gly Lys Ser Val Lys Val Ser Asn Tyr
 45                  50                  55

His Val Ile His Gly Lys Glu Tyr Phe Ile Glu Gly Thr Ala Tyr Pro
 60                  65                  70                  75

Val Gly Asp Ser Lys Ile Gly Lys Ile Tyr His Ser Leu Thr Tyr Gly
                 80                  85                  90

Gly Val Thr Lys Glu Asn Val Phe Asn Val Leu Ser Thr Asp Asn Lys
             95                  100                 105

Asn Tyr Ile Ile Gly Tyr Tyr Cys Lys Tyr Asp Glu Asp Lys Lys Gly
            110                 115                 120

His Gln Asp Phe Val Trp Val Leu Ser Arg Ser Met Val Leu Thr Gly
        125                 130                 135

Glu Ala Lys Thr Ala Val Glu Asn Tyr Leu Ile Gly Ser Pro Val Val
140                 145                 150                 155

Asp Ser Gln Lys Leu Val Tyr Ser Asp Phe Ser Glu Ala Ala Cys Lys
                160                 165                 170

Val Asn Asn Ser Asn Trp Ser His Pro Gln Phe Glu Lys Pro Ala Ser
            175                 180                 185

Leu Ala Glu Ala Lys Val Leu Ala Asn Arg Glu Leu Asp Lys Tyr Gly
        190                 195                 200

Val Ser Asp Tyr Tyr Lys Asn Leu Ile Asn Ala Lys Thr Val Glu
        205                 210                 215

Gly Val Lys Ala Leu Ile Asp Glu Ile Leu Ala Ala Leu Pro
220                 225                 230

<210> SEQ ID NO 18
<211> LENGTH: 183
<212> TYPE: PRT
<213> ORGANISM: Homo sapiens

<400> SEQUENCE: 18

Glu Arg Asp Cys Arg Val Ser Ser Phe Arg Val Lys Glu Asn Phe Asp
 1               5                  10                  15

Lys Ala Arg Phe Ser Gly Thr Trp Tyr Ala Met Ala Lys Lys Asp Pro
             20                  25                  30

Glu Gly Leu Phe Leu Gln Asp Asn Ile Val Ala Glu Phe Ser Val Asp
         35                  40                  45

Glu Thr Gly Gln Met Ser Ala Thr Ala Lys Gly Arg Val Arg Leu Leu
     50                  55                  60

Asn Asn Trp Asp Val Cys Ala Asp Met Val Gly Thr Phe Thr Asp Thr
 65                  70                  75                  80

Glu Asp Pro Ala Lys Phe Lys Met Lys Tyr Trp Gly Val Ala Ser Phe
                 85                  90                  95

Leu Gln Lys Gly Asn Asp Asp His Trp Ile Val Asp Thr Asp Tyr Asp
            100                 105                 110

Thr Tyr Ala Val Gln Tyr Ser Cys Arg Leu Leu Asn Leu Asp Gly Thr
        115                 120                 125

Cys Ala Asp Ser Tyr Ser Phe Val Phe Ser Arg Asp Pro Asn Gly Leu
    130                 135                 140

Pro Pro Glu Ala Gln Lys Ile Val Arg Gln Arg Gln Glu Glu Leu Cys
145                 150                 155                 160

Leu Ala Arg Gln Tyr Arg Leu Ile Val His Asn Gly Tyr Cys Asp Gly
```

```
                      165                 170                 175

Arg Ser Glu Arg Asn Leu Leu
                180

<210> SEQ ID NO 19
<211> LENGTH: 169
<212> TYPE: PRT
<213> ORGANISM: Homo sapiens

<400> SEQUENCE: 19

Gln Ala Phe His Leu Gly Lys Cys Pro Asn Pro Val Gln Glu Asn
 1               5                  10                  15

Phe Asp Val Asn Lys Tyr Leu Gly Arg Trp Tyr Glu Ile Glu Lys Ile
                20                  25                  30

Pro Thr Thr Phe Glu Asn Gly Arg Cys Ile Gln Ala Asn Tyr Ser Leu
            35                  40                  45

Met Glu Asn Gly Lys Ile Lys Val Leu Asn Gln Glu Leu Arg Ala Asp
50                  55                  60

Gly Thr Val Asn Gln Ile Glu Gly Glu Ala Thr Pro Val Asn Leu Thr
65                  70                  75                  80

Glu Pro Ala Lys Leu Glu Val Lys Phe Ser Trp Phe Met Pro Ser Ala
                85                  90                  95

Pro Tyr Trp Ile Leu Ala Thr Asp Tyr Glu Asn Tyr Ala Leu Val Tyr
            100                 105                 110

Ser Cys Thr Cys Ile Ile Gln Leu Phe His Val Asp Phe Ala Trp Ile
        115                 120                 125

Leu Ala Arg Asn Pro Asn Leu Pro Pro Glu Thr Val Asp Ser Leu Lys
    130                 135                 140

Asn Ile Leu Thr Ser Asn Asn Ile Asp Val Lys Lys Met Thr Val Thr
145                 150                 155                 160

Asp Gln Val Asn Cys Pro Lys Leu Ser
                165

<210> SEQ ID NO 20
<211> LENGTH: 174
<212> TYPE: PRT
<213> ORGANISM: Pieris brassicae

<400> SEQUENCE: 20

Asn Val Tyr His Asp Gly Ala Cys Pro Glu Val Lys Pro Val Asp Asn
 1               5                  10                  15

Phe Asp Trp Ser Asn Tyr His Gly Lys Trp Trp Glu Val Ala Lys Tyr
                20                  25                  30

Pro Asn Ser Val Glu Lys Tyr Gly Lys Cys Gly Trp Ala Glu Tyr Thr
            35                  40                  45

Pro Glu Gly Lys Ser Val Lys Val Ser Asn Tyr His Val Ile His Gly
        50                  55                  60

Lys Glu Tyr Phe Ile Glu Gly Thr Ala Tyr Pro Val Gly Asp Ser Lys
65                  70                  75                  80

Ile Gly Lys Ile Tyr His Lys Leu Thr Tyr Gly Gly Val Thr Lys Glu
                85                  90                  95

Asn Val Phe Asn Val Leu Ser Thr Asp Asn Lys Asn Tyr Ile Ile Gly
            100                 105                 110

Tyr Tyr Cys Lys Tyr Asp Glu Asp Lys Lys Gly His Gln Asp Phe Val
        115                 120                 125

Trp Val Leu Ser Arg Ser Lys Val Leu Thr Gly Glu Ala Lys Thr Ala
    130                 135                 140
```

```
Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170
```

ANTICALINS

This application is a divisional of U.S. Ser. No. 12/654,809, filed Jan. 5, 2010, now U.S. Pat. No. 8,158,753, which is a continuation of U.S. Ser. No. 11/224,071, filed Sep. 13, 2005, now U.S. Pat. No. 7,723,476, which is a continuation of U.S. Ser. No. 09/509,444 filed May 21, 2000, now U.S. Pat. No. 7,250,297, which is the national stage of PCT/DE98/02898, filed Sep. 25, 1998, which claims priority from German Application No. 197 42 706.5 filed Sep. 26, 1997.

The lipocalins (Pervaiz and Brew, FASEB J. 1 (1987), 209-214) are a family of small, often monomeric secretory proteins which have been isolated from various organisms, and whose physiological role lies in the storage or in the transport of different ligands as well as in more complex biological functions (Flower, Biochem. J. 318 (1996), 1-14). The lipocalins bear relatively little mutual sequence similarity and their belonging to the same protein structural family was first eluicidated by X-ray structure analysis (Sawyer et al., Nature 327 (1987), 659).

The first lipocalin of known spatial structure was the retinol-binding protein, Rbp, which effects the transport of water-insoluble vitamin A in blood serum (Newcomer et al., EMBO J. 3 (1984), 1451-1454). Shortly thereafter the tertiary structure of the bilin-binding protein, Bbp, from the butterfly *Pieris brassicae* was determined (Huber et al., J. Mol. Biol. 195 (1987), 423-434). The essential structural features of this class of proteins can be illustrated with the help of the spatial structure of this lipocalin, which is schematically reproduced in FIG. 1A. The central element in the folding architecture of the lipocalins is the cylindrical β-pleated sheet structure, the so-called β-barrel, which is made up of eight nearly circularly arranged antiparallel β-strands.

This supersecondary structural element can also be viewed as a "sandwich"-arrangement of two four-stranded β-sheet structures. Additional structural elements are an extended segment at the amino-terminus of the polypeptide chain and an α-helix close to the carboxy-terminus, which itself is followed by an extended segment. These additional features are, however, not necessarily revealed in all lipocalins. For example a significant part of the N-terminal segment is missing in the epididymal retinoic acid-binding protein (Newcomer, Structure 1 (1993), 7-18). Additional peculiar structural features are also known, such as for example membrane anchors (Bishop and Weiner, Trends Biochem. Sci. 21 (1996), 127) which are only present in certain lipocalins.

The β-barrel is closed on one end by dense amino acid packing as well as by loop segments. On the other end the β-barrel forms a binding pocket in which the respective ligand of the lipocalin is complexed. The eight neighbouring antiparallel β-strands there are connected in a respective pairwise fashion by hairpin bends in the polypeptide chain which, together with the adjacent amino acids which are still partially located in the region of the cylindrical β-pleated sheet structure, each form a loop element. The binding pocket for the ligands is formed by these in total four peptide loops. In the case of Bbp, biliverdin IXγ is complexed in this binding pocket. Another typical ligand for lipocalins is vitamin A in the case of Rbp as well as β-lactoglobulin (Papiz et al., Nature 324 (1986), 383-385).

Alignments of the sequences from different representatives of the lipocalin family can be found in, among other publications, the publication by Cowan et al. (Proteins: Struct., Funct., Genet. 8 (1990), 44-61) and in the review article by Flower (FEES Lett. 354 (1994), 7-11). Among the currently many more than 20 different known lipocalins, there exist mainly two human proteins which have already been biochemically characterized in detail: the retinol-binding protein and the apolipoprotein D, ApoD (Yang et al., Biochemistry 33 (1994), 12451-12455). ApoD is especially interesting since it bears a close structural relationship with the Bbp mentioned above (Peitsch and Boguski, New Biologist 2 (1990), 197-206).

A classical example for proteins which selectively bind ligands by way of non-covalent interaction is represented by antibodies, i.e. immunoglobulins. These proteins play a crucial role as reagents in the areas of biotechnology, medicine, bioanalytics as well as in the biological sciences in general. Despite the variety of the given application possibilities in connection with the recognition, binding or separation of ligands, almost exclusively immunoglobulins are currently used for corresponding purposes. In contrast, the application of other proteins with defined ligand-binding characteristics, for example the lectins, has remained restricted to special cases.

Specific antibodies can be specifically produced against diverse host of target structures, so-called haptens or antigens. In addition to the method for producing monoclonal antibodies, which is in the meanwhile generally established, biosynthetic methods have also been more recently employed for) this purpose, for example by using the "phage display" technique (Hoess, Curr. Opin. Struct. Biol. 3 (1993), 572-579; Wells and Lowman, Curr. Opin. Struct. Biol. 2 (1992), 597-604). Once the genetic information for the binding region (variable domains VH and VL) of an immunoglobulin with the desired hapten or antigen specificity is known, the person skilled in the art has at his disposal many genetic engineering techniques using eucaryotic or bacterial expression systems for the production of this antibody, its fragments or hybrid proteins derived from it. Yet the practical application of this class of proteins is still sometimes plagued with disadvantages.

It is for example desirable in medical applications, such as for example tumor imaging or drug targeting (Chester and Hawkins, Trends Biotechnol. 13 (1995) 294-300) to utilize binding domains as small as possible, since with this one expects improved tissue penetration. According to the general view, the Fv-fragment, composed of the variable domain of the light polypeptide chain (VL) and the variable domain of the heavy polypeptide chain (VH) of an antibody, is normally the smallest immunoglobulin fragment which forms a structurally intact antigen-binding site. However, an Fv-fragment typically consists of approximately 240 amino acids, so that such a protein still exhibits relatively large molecular dimensions. Furthermore antibody construction from two different polypeptide chains (light and heavy chain) can lead to undesirable effects. Since a respective pair of coding regions have to be cloned and possibly expressed, recombinant production and handling is complicated in comparison to proteins composed of a single polypeptide chain. In addition, experience has shown that Fv-fragments often possess little proteinchemical stability, since their VL- and VH-domains are bound to each other by non-covalent interactions only. Different strategies have therefore been attempted to stabilize the association of both of the variable domains in the heterodimeric Fv-fragment. One of these methods makes use of the linking of both of the polypeptide chains at the translation al level, wherein so-called scFv-fragments are obtained (Bird and Walker, Trends Biotechnol. 9 (1991), 132-137). However it became apparent that this procedure sometimes leads to other disadvantages, such as for example reductions in the affinity for ligands or an undesired oligomerization behavior (Desplancq et al., Protein Eng. 7 (1994), 1027-1033).

The invention is therefore based on the goal of developing other polypeptide reagents which, like antibodies, exhibit specific binding characteristics for given ligands. According to the invention, this task is met with the anticalins, which are producible starting from polypeptides of the lipocalin family by mutating amino acids which are located in the region of the four peptide loops at the end of the cylindrical β-pleated sheet structure, and which are characterized in that they bind given ligands with a determinable affinity.

A topographical comparison of the course of the polypeptide chain in the protein fold of the lipocalins with the Fv-fragments of the immunoglobulins is shown in FIG. 2. The antigen-binding site in the immunoglobulins is formed by six structurally hypervariable peptide loops, also called complementarity determining regions (CDRs). Both variable domains, VH and VL, contribute three CDRs to the antigen binding site. Both of the variable domains consists each of two β-sheet structures arranged in a layerlike fashion, which form the structurally conserved framework bearing the hypervariable peptide loops. In this way an inner and an outer ring of β-strands arise in, the Fv fragment, wherein two CDRs are fixed between neighbouring strands of the inner ring and four CDRs are fixed between strands of the inner and the outer ring. In contrast, the ligand-binding sites of the lipocalins are constructed more simply. In this case only one ring of 8 antiparallel β-strands exists: the g-barrel. This cyclic β-pleated sheet structure is conserved in the protein fold of the lipocalins. The binding site is formed in the entry region of the g-barrel by the four peptide loops, each of which connects t) two neighbouring β-strands with one another. These peptide loops can vary significantly in their structure between the individual members of the lipocalin family.

Despite the apparent analogy in the structure of the immunoglobulins and the lipocalins, i.e. conserved framework regions on the one hand and hypervariable, specificity-determining segments on the other, there exists one essential difference between these two proteins classes. Namely, while approximately 100 million different antibodies circulate in the human body and are continually generated, the same organism produces only a few lipocalins, such as for example Rbp or ApoD mentioned above. Whereas antibodies with new antigen specificities constantly arise in the immune system of a mammal through somatic gene recombination and mutation, the lipocalins have in contrast remained mostly conserved in the course of evolution in the structure and function of their respective ligand-binding sites. Rbp, the amino acid sequence of which is known from different organisms, serves as an example of this. Sequence comparison of human Rbp (SWISS-PROT Databank Access Number P02753) with, for example, porcine Rbp (SWISS-PROT Databank Access Number P27485) and with bovine Rbp (SWISS-PROT Databank Access Number P18902) reveals the presence of only 13 and 14 differences, respectively. In addition, all of these amino acid substitutions are located in the spatial structure distant from the binding site for retinol (see FIG. 13 in the publication of Crown et al., supra).

In the method according to the invention this gap between the functional characteristics of antibodies and lipocalins is closed in that one or more of the four peptide loops forming the ligand-binding site of a lipocalin is subjected to mutagenesis, followed by choosing, i.e. selecting those protein variants (muteins), which exhibit the desired binding activity for a given ligand. The lipocalin muteins obtained in this way are termed anticalins.

The following explains by way of example, namely by way of Bbp, what is to be understood by the term peptide loops in this invention in view of the polypeptide sequences. The four peptide loops of the lipocalins which, according to the inventive production of the anticalins, are modified in their sequence by mutagenesis, are characterized by those segments in the linear polypeptide sequence comprising amino acid positions 28 to 45, 58 to 69, 86 to 99 and 114 to 129 of Bbp. Each of these sequence segments begins before the C-terminus of one of the conserved β-strands at the open side of the β-barrel, includes the actual peptide hairpin, and ends after the N-terminus of the likewise conserved E-strand which follows in the sequence.

With the help of published sequence alignments or those which are performable by the person skilled in the art, or of structural superpositions, the definition of the sequence positions given for Bbp can be assigned to other lipocalins. For example, one can read off the sequence alignments reproduced in FIG. 3, which correspond to the published alignment of Peitsch and Boguski (New Biologist 2 (1990), 197-206), that the four peptide loops in the case of ApoD include the amino acid positions 28 to 44, 59 to 70, 85 to 98 and 113 to 127. It is also possible to identify the corresponding peptide loops in new lipocalins which are suitable for an inventive mutagenesis in the same way.

In some cases, the relatively weak sequence homology of the lipocalins may prove to be problematic in the determination of the conserved β-strands. It is therefore crucial that the polypeptide sequence be capable of forming the cyclic β-pleated sheet structure made of 8 antiparallel β-strands. This can be determined by employing methods of structural analysis such as protein crystallography or multidimensional nuclear magnetic resonance spectroscopy.

In other lipocalins, such as for example ApoD or Rbp, the sequence segments suitable for mutagenesis can easily be longer or shorter than that of Bbp (see FIG. 3) based on the individually varying structure of the peptide loops. It can even be advantageous to additionally modify the length of sequence segments by deletion or insertion of one or more amino acids. In a preferred embodiment of the invention, those amino acid positions in these sequence segments are mutated which correspond to sequence positions 34 to 37, 58, 60, 69, 88, 90, 93, 95, 97, 114, 116, 125, and 127 of Bbp. These amino acid positions are emphasized in FIGS. 1B and 3. Correspondingly, in the case of ApoD, the sequence positions 34 to 37, 59, 61, 70, 87, 89, 92, 94, 96, 113, 115, 123 and 125 are preferred for mutagenesis. However, for the production of anticalins not all of the sequence positions given here have to be subjected to mutagenesis.

Of course, other lipocalins besides those examples cited here are also suitable as an underlying structure for the production of anticalins. Preferably, the lipocalins Rbp, Bbp or ApoD, which presently have already been exhaustively studied biochemically, are used. The use of lipocalins of human origin is especially preferred for the production of anticalins. This especially applies when an application of the resulting anticalin(s) is intended for humans since, for example in diagnostic or therapeutic applications in vivo, a minimumal immunogenic effect is to be expected as compared to lipocalins from other organisms. However, other lipocalins as well as lipocalins which, possibly, have yet to be discovered can prove to be especially advantageous for the production of anticalins. Artificial proteins with a folding element which is structurally equivalent to the β-barrel of the lipocalins can also be used.

Preferably the anticalins according to the invention should be able to bind the desired ligand with a determinable affinity, i.e. with an affinity constant of at least $10^5$ $M^{-1}$. Affinities lower than this are generally no longer exactly measurable with common methods and are therefore of secondary importance for practical applications. Especially preferred are anticalins which bind the desired ligand with an affinity of at least $10^6$ $M^{-1}$, corresponding to a dissociation constant for the complex of 1 μM. The binding affinity of an anticalin to the desired ligand can be measured by the person skilled in the art by a multitude of methods, for example by fluorescence titration, by competition ELISA or by the technique of surface plasmon resonance.

The lipocalin cDNA, which can be produced and cloned by the person skilled in the art by known methods, can serve as a starting point for mutagenesis of the peptide loop, as it was for example described for Bbp (Schmidt and Skerra, Eur. J. Biochem. 219 (1994), 855-863). Alternatively, genomic DNA can also be employed for gene synthesis or a combination of these methods can be performed. For the mutagenesis of the amino acids in the four peptide loops, the person skilled in the art has at his disposal the various known methods for site-directed mutagenesis or for mutagenesis by means of the polymerase chain reaction. The mutagenesis method can, for example, be characterized in that mixtures of synthetic oligodeoxynucleotides, which bear a degenerate base composition at the desired positions, can be used for introduction of the mutations. The implementation of nucleotide building blocks with reduced base pair specificity, as for example inosine, is also an option for the introduction of mutations into the chosen sequence segment or amino acid positions. The procedure for mutagenesis of ligand-binding sites is simplified as compared to antibodies, since for the lipocalins only four instead of six sequence segments—corresponding to the four above cited peptide loops—have to be manipulated for this purpose.

In the methods of site-directed random mutagenesis implementing synthetic oligodeoxynucleotides, the relevant amino acid positions in the lipocalin structure which are to be mutated can be determined in advance. The ideal selection of the amino acid positions to be mutated can depend on the one hand on the lipocalin used, and on the other hand on the desired ligand. Here, it can be useful to maintain the total number of mutated amino acid positions within a single experiment low enough such that the collection of variants obtained by mutagenesis, i.e. the so-called library, can in its totality or, at least in a representative selection therefrom, be realized as completely as possible in its combinatorial complexity, not only at the level of the coding nucleic acids, but also at the level of the gene products.

It should be possible to choose the amino acid positions to be mutated in a meaningful way especially when structural information exists pertaining to the lipocalin itself which is to be used, as in the case with Rbp and Bbp or at least pertaining to a lipocalin with a similar structure, as for example in the case of ApoD. The set of amino acid positions chosen can further depend on the characteristics of the desired ligand. In the case of the small hapten-like ligand, it can for example be useful to subject especially those amino acid positions at the center of the ligand binding pocket to mutation, in other words those in or nearby the region of the β-barrel. In contrast, in the case of a larger antigen-like ligand, mutagenesis should also effect those amino acid positions in the peptide loops which are arranged in an exposed manner on the protein surface, and which are located more in the middle of the corresponding sequence segments. Apart from such a functional view, it can also prove advantageous to exclude single amino acid positions in the region of the ligand-binding pocket from mutagenesis if these for example prove to be essential for the folding efficiency or the folding stability of the protein.

One of the many applicable methods for the introduction of mutations in the region of the four peptide loops of a lipocalin is based on the use of four oligodeoxynucleotides, each of which is derived from one of the four corresponding sequence segments to be mutated. In the production of these oligodeoxynucleotides, the person skilled in the art can employ mixtures of nucleic acid building blocks for the synthesis of those nucleotide triplets which correspond to the amino acid positions to be mutated, so that codons or anticodons randomly arise for all amino acids or, according to the genetic code and to the composition of this mixture, for a selection of the desired amino acids at this position.

For example, the first oligodeoxynucleotide corresponds in its sequence—apart from the mutated positions—at least partially to the coding strand for the peptide loop, which is located in the polypeptide sequence of the lipocalin at the most N-terminal position. Accordingly, the second oligodeoxynucleotide corresponds at least partially to the non-coding strand for the second sequence segment following in the polypeptide sequence. The third oligodeoxynucleotide corresponds in turn at least partially to the coding strand for the corresponding third sequence segment. Finally, the fourth oligodeoxynucleotide corresponds at least partially to the non-coding strand for the fourth sequence segment. A polymerase chain reaction can be performed with the respective first and second oligodeoxynucleotide as well as with the respective third and fourth oligodeoxynucleotide by using the nucleic acid which codes for the lipocalin and/or its complementary strand as a template.

The amplification products of both of these reactions can be combined by various known methods into a nucleic acid which comprises the sequence from the first to the fourth sequence segment, and which bears the mutation at the chosen amino acid position. To this end, both of the products can for example be subjected to a new polymerase chain reaction using flanking oligodeoxynucleotides as primers as well as one or more mediator nucleic acid molecules which contribute the sequence between the second and the third sequence segment. This procedure is schematically reproduced in FIG. 4. In the choice of the number of the oligodeoxynucleotides used for the mutagenesis and their arrangement within the gene sequence of the lipocalin, the person skilled in the art furthermore has numerous alternatives at his disposal.

The nucleic acid molecules which code for the sequence region with the four peptide loops of a lipocalin and which contain mutations at the chosen positions can be connected by ligation with the missing 5'- and 3'-sequences of a nucleic acid coding for the lipocalin, and can be cloned in a known host organism. A multitude of procedures are at one's disposal for the ligation and the cloning. For example, in the course of an amplification, synthetic nucleic acid molecules with restriction endonuclease recognition sequences, which are also present at the corresponding positions in the nucleic acid sequence for the lipocalin, can be attached at both ends of the nucleic acid to be cloned so that a ligation is made possible following hydrolysis with the corresponding restriction enzyme.

The present invention relates also to the directed mutagenesis of single amino acid positions within or without the four peptide loops, for example in order to simplify the subcloning of the mutated lipocalin gene or its parts by incorporating cleavage sites for certain restriction enzymes. For example the mutations Asn21 to Gln and Lys135 to Met can be introduced in the Bbp gene in order to simplify the cloning of the mutated gene segment via two new BstXI restriction sites at these positions. The present invention also relates to the directed introduction of mutations within or without the four peptide loops in order to improve certain characteristics of the anticalin, for example its folding stability or folding efficiency or its resistance to proteases. For example, cleavage of Bbp into two fragments, which otherwise arises upon its production in *E. coli*, is thus suppressed by the amino acid substitution Lys87 to Ser. In addition, an oligomerization of the original Bbp can be avoided by the mutation of Asn1 to Asp. Also, by exchange of Cys116 to Ser in ApoD, its covalent crosslinking with other proteins can be prevented and its monomeric structure can be stabilized.

In a preferred embodiment of the invention, the Bbp variant with the substitution Lys87 to Ser serves correspondingly as the basic structure for the production of anticalins. Bbp variants with the substitutions Asn1 to Asp, Asn21 to Gln, Lys135 to Met and Lys87 to Ser are especially preferred for use in the production of anticalins.

Longer sequence segments within the gene coding for the lipocalin can also be subjected to random mutagenesis via known methods, for example by use of the polymerase chain reaction under conditions of increased error rate, by chemical mutagenesis or by using bacterial mutator strains (Low et al., J. Mol. Biol. 260 (1996), 359-368). Such methods can also be used for the further optimization of the ligand affinity or ligand specificity of an anticalin which has already been produced. Mutations which possibly occur outside of the four loop regions can often be tolerated or can even prove advantageous if they for example contribute to an improved folding efficiency or folding stability of the anticalin.

After having brought the coding nucleic acid sequences subjected to mutagenesis to expression, the clones carrying the genetic information for anticalins which bind a given ligand can be selected from the differing clones of the library obtained. Known expression strategies and selection strategies can be implemented for the selection of these clones. Methods of this sort have been described in the context of the production or the engineering of recombinant antibody fragments, such as the "phage display" technique or "colony screening" methods (Skerra et al., Anal. Biochem. 196 (1991), 151-155).

An embodiment of the "phage display" technique (Hoess, supra; Wells and Lowman, supra; Kay et al., Phage Display of Peptides and Proteins—A Laboratory Manual (1996), Academic Press) is given here as an example of an selection method according to the invention for anticalins with the desired binding characteristics. The various other possible embodiments of the "phage display" technique are hereby incorporated into the disclosure by reference. For the exemplary selection method, phasmids are produced which effect the expression of the mutated lipocalin structural gene as a fusion protein with a signal sequence at the N-terminus, preferably the OmpA-signal sequence, and with the coat protein pIII of the phage M13 (Model and Russel, in "The Bacteriophages", Vol. 2 (1988), Plenum Press, New York, 375-456) or fragments of this coat protein, which are incorporated into the phage coat, at the C-terminus. The C-terminal fragment ΔpIII of the phage coat protein, which contains only amino acids 217 to 406 of the natural coat protein pIII, is preferably used to produce the fusion proteins. Especially preferred is a C-terminal fragment from pIII in which the cysteine residue at position 201 is missing or is replaced by another amino acid.

The fusion protein can contain other components such as for example an affinity tag or an epitope sequence for an antibody which allows the immobilization or the later purification of the fusion protein or its parts. Furthermore, a stop codon, can be located between the region coding for the lipocalin or anticalin and the gene segment for the coat protein or its fragment, which stop codon, preferably an amber stop codon, is at least partially translated into an amino acid during translation in a suitable suppressor strain.

Phasmids here denote plasmids which carry the intergenetic region of a filamentous bacterial phage, such as for example M13 or f1 (Beck and Zink, Gene 16 (1981), 35-58) or a functional part thereof, so that during superinfection of the bacterial cells with a helper phage, for example M13K07, VCS-M13 or R408, one strand of the circular phasmid DNA is packaged with coat proteins and is exported into the medium as so-called phagemid. On the one hand this phagemid has the lipocalin mutein encoded by the respective phasmid built into its surface as a fusion with the coat protein pIII or its fragment, wherein the signal sequence of the fusion protein is normally cleaved off. On the other hand it carries one or more copies of the native coat protein pIII from the helper phage and is thus capable of infecting a recipient—generally a bacterial strain carrying an F- or F'-plasmid. In this way a physical coupling is ensured between the packaged nucleic acid carrying the genetic information for the respective lipocalin mutein or anticalin, and the encoded protein which is at least partially presented in functional form on the surface of the phagemid.

The vector pBBP20 (FIG. 5) can for example be used in the construction of the phasmisd with the sequences coding for the Bbp muteins. An analogeous vector is produced for the selection of anticalins starting from another lipocalin, in that the DNA-sequence which codes for this lipocalin or its mutein is inserted into the vector pBBP20 instead of the sequence coding for Bbp. In the case of Bbp or its muteins, the nucleic acid coding for the peptide loops can for example be inserted into the vector pBBP20 via both of the BstXI-restriction sites. Recombinant phasmids are incorporated by transformation into the *E. coli* strain, for example XL1-blue (Bullock et al., BioTechniques 5 (1987), 376-379) or TG1. In this way, clones are made which can produce many different lipocalin muteins as fusion proteins.

This library, i.e. the collection of the clones obtained, is subsequently superinfected in liquid culture according to known methods with an M13-helper phage. After this infection the incubation temperature of the culture can be reduced for production of the phagemids. Preferred incubation temperatures are those in which the optimal folding of the lipocalin mutein as a component of the fusion protein with the phage coat protein or its fragment is expected. During or after the infection phase the expression of the gene for the fusion protein with the lipocalin mutein can be induced in the bacterial cells. The induction conditions are chosen such that a substantial fraction of the phagemids produced presents at least one lipocalin mutein. The phagemids are isolated after a culture incubation phase of for example 6 to 8 hours. Various methods are known for isolation of the phagemids, such as for example precipitation with polyethylene glycol.

The isolated phasmids can be subjected to a selection by incubation with the desired ligand, wherein the ligand is present in a form allowing at least a temporary immobilization of those phagemids carrying anticalins with the desired binding activity as fusion proteins in their coat. Among the various embodiments known to the person skilled in the art, the ligand can for example be conjugated with a carrier protein such as serum albumin and be bound via this carrier protein to a protein binding surface, for example polystyrene. Microtiter plates suitable for ELISA techniques or so-called "immuno-sticks" can preferably be used for this immobilization of the ligand. Alternatively, conjugates of the ligand can also be implemented with other binding groups such as for example biotin. The ligand can then be immobilized on surfaces which selectively bind this group, such as for example microtiter plates or paramagnetic particles coated with streptavidin or avidin.

Protein-binding sites present on the surfaces which are charged with ligands can be saturated with blocking solutions known for ELISA-methods. The phagemids are for example subsequently brought in contact in a physiological buffer with the ligand immobilized on the surface. Unbound phagemids are removed by multiple washings. The phagemid particles remaining on the surface are subsequently eluted. For elution, the free ligand can be added as a solution. But the phagemids can also be eluted by addition of proteases or under moderately denaturing conditions, for example in the presence of acids, bases, detergents or chaotropic salts. A preferred method is the elution using buffers of pH 2.2, wherein the eluate is subsequently neutralized.

Afterwards, E. coli cells are infected with the eluted phagemids using generally known methods. The nucleic acids can also be extracted from the eluted phagemids and be incorporated into the cells in another manner. Starting from the E. coli clones obtained in this way, phagemids are in turn generated by superinfection with M13-helper phages according to the method described above and the phagemids propagated in this way are once again subjected to a selection on the surface with the immobilized ligand. Multiple selection cycles are often necessary in order to obtain the phagemids with the anticalins in enriched form. The number of selection cycles is preferably chosen so that in the subsequent functional analysis at least 0.1% of the clones studied produce lipocalin muteins with detectable or determinable affinity for the given ligand. Depending on the size, i.e. the complexity, of the library employed, 2 to 8 cycles are typically required to this end.

For the functional analysis of the selected muteins, an E. coli strain is infected with the phagemids obtained from the selection cycles and the corresponding double stranded phasmid DNA is isolated. Starting from this phasmid DNA or also from the single-stranded DNA extracted from the phagemids, the nucleic acid sequences of the selected lipocalin muteins can be determined by the methods common for this purpose and the amino acid sequence can be derived therefrom. The mutated region or the sequence of the entire lipocalin mutein or anticalin can be subcloned in another expression vector and expressed in a suitable host organism. pBBP21 can for example be used as the expression vector and the expression with pBBP21 derivatives can be performed in E. coli strains, for example E. coli-TG1. The anticalins produced by genetic engineering can be purified by various proteinchemical methods. The anticalins produced for example with pBBP21 carry the affinity peptide Strep-Tag II (Schmidt et al., J. Mol. Biol. 255 (1996), 753-766) at their C-terminus and can therefore preferably be purified by streptavidin affinity chromatography.

The selection can also be carried out by means of other methods. Many corresponding embodiments are known to the person skilled in the art or are described in the literature. A combination of methods can also be applied. For example clones selected or at least enriched by "phage display" can additionally be subjected to a "colony screening". This procedure has the advantage that individual clones can directly be isolated with respect to the production of anticalins with detectable binding affinity for a ligand.

In addition to the use of E. coli as host organism in the "phage display" technique or the "colony screening" method, other bacterial strains, yeast or also insect cells or mammalian cells can for example be used for this purpose. In addition to the selection of an anticalin from a primary library produced starting from a coding nucleic acid sequence for a lipocalin, comparable methods can also be applied in order to optimize an anticalin with respect to the affinity or specificity for the desired ligand by repeated, optionally limited mutagenesis of its coding nucleic acid sequence.

It is surprising that anticalins can be isolated with the method according to the invention which show high affinity to a given ligand. Binding constants of more than $10^6$ $M^{-1}$ were determined for various fluorescein derivatives with the anticalins described in the examples. These affinity values are of the same order of magnitude as the affinities of the lipocalins to their natural ligands, for example of Rbp to vitamin A (Cogan et al., Eur J. Biochem. 65 (1976), 71-78). In contrast to the natural lipocalin ligands, which are normally water-insoluble and chemically unstable, fluorescein is a relatively hydrophilic compound, which has also been used in immunological studies as a hapten with model character (Voss, Fluorescein Hapten: An Immunological Probe (1984), CRC Press). Moreover fluorescein bears no structural relationship whatsoever to biliverdin IX, the original ligand of Bbp.

Such affinities attainable with the anticalins for novel ligands are comparable with the affinities which are known for antibodies from the secondary immune response. Furthermore, there additionally exists the possibility to subject the anticalins produced to a further, optionally partial random mutagenesis in order to select variants of even higher affinity from the new library thus obtained. Corresponding procedures have already been described for the case of recombinant antibody fragments for the purpose of an "affinity maturation" (Low et al., supra; Barbas and Burton, Trends Biotechnol. 14 (1996), 230-234) and can also be applied to anticalins in a corresponding manner by the person skilled in the art.

Surprisingly it furthermore turned out that the four peptide loops forming the ligand binding pocket of the lipocalins exhibit high tolerance for amino acid substitutions, without the folding of the polypeptide chain in the isolated anticalins being substantially affected by it. Accordingly, it is possible to generate anticalins which have binding pockets with diverse surface properties so that the molecular recognition of a wide variety of ligands, also of peptides or polypeptides as well as other macromolecules, can be realized.

If the genetic information for an anticalin has first been obtained or its amino acid sequences is known, then it can be produced with generally known genetic engineering methods. Preferred are methods for the production of anticalins, wherein the anticalin, a fragment of the anticalin or a fusion protein of the anticalin and another polypeptide is produced in a bacterial or eucaryotic host organism by means of genetic engineering methods starting from the nucleic acid coding for the anticalin, and is isolated from this host organism or its culture. The fact that, in doing so, normally only one structural gene has to be brought to expression represents a significant simplification in comparison to antibodies or their fragments.

A multitude of host organisms, such as E. coli and other gram negative or also gram positive bacteria, yeast and other eucaryotic cells can be employed for the recombinant production. The choice between various expression strategies is also possible. For example, secretion with a suitable signal sequence in the host organism E. coli, as described in the examples, leads to the correctly folded, functional protein in which the disulfide bonds are formed. On the other hand it is also possible to produce an anticalin in the cytosol of a bacterial cell and, in the case that the lipocalin is not functionally folded in the cytosol, to functionally refold it later in vitro. Even a refolding from aggregates which accumulate during the secretion in the periplasm of the bacterium is possible.

Anticalins made by genetic engineering can be purified by means of a multitude of established methods. The suitability of the method depends on the respective host organism used, the expression strategy and other factors which are known to the person skilled in the art experienced in the expression and purification of recombinant proteins. The purification can optionally be simplified in that the anticalin is fused with one or more peptide sequences. For the fusion, such peptides or proteins are preferably used which confer on the resulting recombinant protein an affinity to certain column materials. Such fusions should not negatively influence the function of the anticalin or must for example be cleavable by the insertion of a suitable protease clipping site. Typical examples for fusion partners given here are oligohistidine-tags, the Strep-Tag or the Strep-Tag II, glutathione S-transferase, maltose-binding protein or the albumin-binding domain of protein G. Anticalins can just as well be purified via their respective ligand-binding sites by means of affinity chromatography on a column matrix with the immobilized matching ligand, or suitable derivatives of this ligand. Compared to recombinant antibody fragments, the fact that the anticalins are composed of a single polypeptide chain is advantageous in the purification since no precautions have to be undertaken in order to ensure the intact association of subunits.

The structure of an anticalin can be additionally modified for the purpose of improved production, purification or applicability. For example, the N- or the C-terminal peptide segment not part of the β-barrel structure can be removed. Disulfide bonds present can be eliminated by substitution of the cysteine residues or new disulfide bonds can be introduced at another site. Free cysteine residues, such as the residue 116 in ApoD, can be removed when they interfere with, for example, the production or the stability of the anticalin. Optionally, cysteine residues can also be newly introduced in order to prepare, for example, corresponding protein conjugates by chemical coupling with other components. Binding sites for further ligands, such as for example metal ions, can also be built into the anticalin outside of the actual ligand-binding pocket. Finally, fusion proteins of anticalins and other polypeptides, proteins or protein domains can be made for other purposes than protein production or purification by means of methods known to the person skilled in the art. Preferably, the fusion can take place at the N-terminus or also at the C-terminus of the anticalin.

Such fusions can be suitable to confer new characteristics on the anticalin, such as for example enzymatic activity or affinity for other molecules such as proteins, macromolecules or low molecular weight ligands. For example, fusions with enzymes are possible which catalyse chromogenic or fluorogenic reactions or which can serve for the liberation of cytotoxic agents. Further examples of fusion partners which can be advantageous in practice are binding domains such as the albumin-binding domain of protein G, protein A, antibody fragments, oligomerizing domains, toxins or also anticalins with different or the same ligand specificity. Alternatively to the production of the fusion proteins, conjugates of anticalins and proteins, nucleic acids or almost any biomolecules and chemical compounds can be made by means of methods known to the person skilled in the art.

Similar to antibodies or their fragments, anticalins and their derivatives can be employed in many areas. Anticalins are preferably used for binding to a solid phase, so that the ligand of the anticalin or a conjugate or fusion protein of this ligand can be immobilized or separated. Further preferred is the use of anticalins for labelling with an enzyme, an antibody or a radioactive substance or another group with a biochemical activity or with defined binding characteristics, so that the ligand of the anticalin or a conjugate or fusion protein of this ligand can be detected or brought in contact with it. Anticalins can serve for example in the verification of chemical structures by means of established bioanalytic methods such as ELISA or Western Blot, in microscopy or immunosensorics. Here, the detection signal can either be generated directly by use of a suitable anticalin conjugate or anticalin fusion protein, or indirectly with detection of the bound anticalin by means of an antibody directed against it or for example by using an affinity tag.

Preferred ligands for anticalins are on the one hand chemical compounds in free or conjugated form which exhibit the characteristics of an immunological hapten, and on the other hand peptides, polypeptides or other macromolecules as well as corresponding conjugates thereof. An interesting area of application is the use of anticalins in order to detect non-radioactively labelled biomolecules, especially nucleic acids. For example, chemically reactive fluorescein derivatives for the labelling of proteins and nucleic acids are commercially available, and methods are also known for the incorporation of fluorescein groups during the synthesis or replication of nucleic acids. Correspondingly modified nucleic acids can be used as specific gene probes and can be subsequently detected with the anticalins described in the examples.

Anticalins can also exert a quenching effect on the fluorescence of the ligands bound by them, such as for example fluorescein. For such anticalins, there arise promising possible applications in biophysical studies. For example, the fluorescence quenching effect of an anticalin can be exploited in a similar manner as with certain antibodies against fluorescein in order to determine the orientation of a membrane protein labelled with fluorescein in the membrane bi-layer. A further area of application is in the studying of the dynamics of ligand/receptor interactions on the cell surface, wherein the ligand is labelled with a fluorescein group. Various other applications in which the fluorescence quenching of fluorescein or other fluorescing compounds plays a role are also possible. For example, an anticalin can be employed in order to avoid a disturbing background intensity by excess fluorescein-labelled reagent in the fluorescence microscopy of cells.

There exist numerous possible applications for the anticalins in medicine. In addition to their use in diagnostics, anticalins can also be prepared which bind for example tissue- or tumor-specific cellular surface molecules. Corresponding anticalins can be employed in conjugated form or as fusion proteins for "tumor imaging" or directly for cancer therapy. In making such anticalins it can be useful to start from a human lipocalin, such as for example Rbp or ApoD. In doing so, the small size of the anticalins or their derivatives has novel and advantageous characteristics as compared to antibodies.

BRIEF DESCRIPTION OF THE DRAWINGS

The invention is further illustrated by the following examples and the attached drawings in which:

FIG. 1 schematically represents the three-dimensional molecular structure of Bbp with its ligand biliverdin IX, (A) and depicts the spatial position of those amino acids (B) which are preferably the object of the mutagenesis for the preparation of anticalins;

FIG. 2 compares the topography of the polypeptide chain for the ligand binding sites of antibodies (A) and of lipocalins (B) with each other;

FIG. 3 aligns the amino acid sequences (SEQ ID NOS 18-20) of various lipocalins;

FIG. 4 schematically illustrates the production of the library of lipocalin muteins at the nucleic acid level;

FIG. 6 schematically depicts the expression vectors pBBP21 (A) and pBBP22 (B);

FIG. 1 shows the crystal structure of Bbp (File 1BBP from the Brookhaven Protein Databank; Molecule A), which was graphically represented with the help of the program MOL-SCRIPT (Kraulis, J. Appl. Cryst. 24 (1991), 946-950). In (A) the bound ligand as well as disulfide bonds in the polypeptide are depicted as "ball and stick" (carbon: black; nitrogen, sulfur: dark grey; oxygen: light grey). The individual E-strands are depicted as ribbons and the α-helix is depicted as a spiral. The cup-like shape of the ligand-binding site can be recognized at the top on the upper end of the E-barrel formed by the eight antiparallel β-strands. In (B) the $C^\alpha$-positions of the amino acids are depicted in connection with one another along the polypeptide chain. The N- and C-terminus of the polypeptide is labelled. The black-colored $C^\alpha$-positions axe designated with the sequence numbers and denote the positions of the mutated amino acids in the structure of Bbp according to the examples.

FIG. 2 shows a view from above (A) onto the antigen-binding site in the Fv-fragment of an immunoglobulin which is formed together by the variable domains VL and VH, and (B) onto the ligand-binding site of a lipocalin. The β-strands are each arranged approximately perpendicular to the plane of the paper and are represented as bars. The six CDRS (L1, L2, L3, H1, H2, H3) in the immunoglobulin as well as the four peptide loops in the lipocalin connect each two β-strands with one another. The other connecting segments and structural elements are omitted.

FIG. 3 shows a sequence comparison (amino acids are given in single letter code) between the bilin-binding protein (SWISS-PROT Data Bank Access Number P09464), human apolipoprotein D (SWISS-PROT Data Bank Access Number P05090) and the retinol-C) binding protein (SWISS-PROT Data Bank Access Number P02753) in the form of the mature polypeptide. The eight segments in the region of the S-barrel corresponding to the conserved β-strands, which exhibit high similarity in the crystal structures of Bbp and Rbp, are emphasized by underlining. The loop regions in which amino acids are preferably exchanged are marked below the sequence of Bbp by double underlining. Those positions in Bbp which are mutated in the examples are additionally labelled with asterisks. The alignment between the sequences of Bbp and ApoD corresponds to that in the publication of Peitsch and Boguski (New Biologist 2 (1990), 197-206).

FIG. 4 schematically shows a strategy for the concerted mutagenesis of 16 selected amino acid positions in the Bbp by repeated application of the polymerase chain reaction (PCR). For each of the four peptide loops of the lipocalin in which the amino acids are to be mutated, an oligodeoxynucleotide was synthesized, (SEQ ID NO:1, SEQ ID NO:2, SEQ ID NO:3 and SEQ ID NO:4), wherein the respective mixtures of the building blocks given in the sequence protocol were employed at the mutation sites. Due to the composition chosen, from the altogether three possible stop codons only the amber stop codon, TAG, could possibly arise at all of the mutated codons, which is translated as glutamine in the *E. coli* supE-strains XL1-blue or TG1 used for gene expression. For certain applications, for example for gene expression in other bacterial strains or organisms, such a nonsense codon, when it arises in the structural gene for a selected anticalin, can be substituted by a glutamine-encoding codon by the person skilled in the art, for example via site-directed mutagenesis. A nucleic acid fragment with 159 base pairs was amplified (Step 1, A) with the primers SEQ ID NO:1 and SEQ ID NO:2 using the pBBP20-plasmid-DNA (SEQ ID NO:10) containing the Bbp-structural gene as template. Parallel to this, a nucleic acid fragment with 164 base pairs was amplified (Step 1, B) with the primers SEQ ID NO:3 and SEQ ID NO:4, also using pBBP20 as template. The mixture of both of these fragments served as template in a second amplification step in the presence of an oligodeoxynucleotide SEQ ID NO:5 hybridizing with both of these fragments as well as the two flanking PCR primers SEQ ID ND: 6 and SEQ ID NO:7, wherein a gene fragment of 371 base pairs was obtained. This fragment contained all 16 mutated codons and was subsequently cloned using both of the BstXI-restriction sites in the vector pBBP20. The use of these two restriction sites, the special arrangement of which led to two non-compatible overhanging DNA-ends during the restriction digest, enabled a particularly efficient ligation. Both of these amino acid substitutions Asn21 to Gln and Lys135 to Met with respect to the original sequence had already been accomplished in order to introduce both of the BstXI restriction sites into the Bbp structural gene.

FIG. 5 shows a drawing of pBBP20. This vector codes for a fusion protein from the OmpA signal sequence, a modified Bbp with the four amino acid substitutions Asn1 to Asp, Asn21 to Gln, Lys87 to Ser and Lys135 to Met, the Strep-Tag II affinity tag and a shortened form of the coat protein pIII from M13, comprising the amino acids 217 to 406 (pIII). The structural gene is subject to the transcriptional control of the tetracycline promoter/operator ($tet^{P/O}$) and ends at the lipoprotein transcription terminator ($t_{lpp}$)). Further elements of the vector are the replication origin (ori), the intergenic region of the filamentous bacterophage f1 (f1-IG), the ampicillin resistance gene (bla) coding for β-lactamase and the tetracycline repressor gene (tetR). An amber stop codon, which is partially read through in an amber suppressor host strain, is located between the coding region for Bbp with OmpA signal sequence and the Strep-Tag II as well as the coding region for the truncated phage coat protein pIII. Both the BstXI-restriction sites used for the cloning of the mutated gene cassette and the restriction sites flanking the structural gene are labeled. A relevant segment from the nucleic acid sequence of pBBP20 is reproduced together with the encoded amino acid sequence (SEQ ID NO: 14) in the sequence protocol as SEQ ID NO: 10. The segment begins with a hexanucleotide sequence obtained by ligation of an XbaI overhang with an SpeI overhang complementary thereto, and ends with the HindIII restriction site. The vector elements outside of this region are identical with the vector pASK75, the complete nucleotide sequence of which is given in the published German patent publication DE 44 17 598 A1.

FIG. 6 shows a drawing of pBBP21 (A) and of pBBP22 (B). pBBP21 codes for a fusion protein made of the OmpA signal sequence, a modified Bbp according to FIG. 5 and the Strep-Tag II affinity tag. This structural gene is followed by the dsbC-structural gene (including its ribosomal binding site) from *E. coli* (Zapun et al., Biochemistry 34 (1995), 5075-5089) as a second cistron. The artificial operon formed in this way is subject to the common transcriptional control of the tetracycline-promoter/operator ($tet^{P/O}$) and ends at the lipoprotein transcription terminator ($t_{lpp}$). All further genetic elements are identical with pBBP20 according to FIG. 5. The overproduction of the bacterial disulfide isomerase in connection with the cosecretion can support the formation of the correct disulfide bridges in the lipocalin and can thus increase the yield of correctly folded polypeptide. However, the production of the lipocalin or of the anticalins is also possible without this precaution. A relevant segment from the nucleic acid sequence of pBBP21 is reproduced together with the encoded amino acid sequences (SEQ ID NOS 15 & 16) in the sequence protocol as SEQ ID NO: 11. The segment begins with the XbaI restriction site and ends with a hexanucleotide which was obtained by ligation of a blunt end with a filled-in HindIII end, whereby the original HindIII cleavage site was lost. The vector elements outside of this region are identical to the vector pASK75, the complete nucleotide sequence of which is given in the German patent publication DE 44 17 598 A1. pBBP22 codes for a fusion protein made of the OmpA-signal sequence, a modified Bbp according to FIG. 5, the Strep-Tag II affinity tag, and an albumin-binding domain (abd) of protein G from *Streptococcus* (Kraulis et al., FEBS Lett. 378 (1996), 190-194). All further genetic elements are identical with pBBP2D. A relevant segment from the nucleic acid sequence of pBBP22 is reproduced together with the encoded amino acid sequence (SEQ ID NO: 17) in the sequence protocol as SEQ ID NO: 12. The segment begins with the XbaI-restriction site and ends with the HindIII restriction site. The vector elements outside of this region are identical with the vector pASK75, the complete nucleotide sequence of which is given in the German patent publication DE 44 17 598 A1.

FIG. 7 shows a graphical representation of the data from Example 7, in which a synthesized peptide epitope of the hepatitis C-virus was detected with the anticalins HepC1 (squares) and HepC4 (circles) in an ELISA. The values obtained with Bbp (triangles) are plotted for comparison. "C" represents the relative protein concentration within each dilution series.

FIG. 8 shows a graphical representation of the data from Example 8, in which different concentrations of the anticalin FluA are added to a 1 µM solution of fluorescein. The fluorescence intensities were measured at an excitation wavelength of 490 nm and an emission wavelength of 512 nm and were plotted against the respective total concentration of the anticalin in the mixture. The data points were finally fitted by a curve.

EXAMPLES

Example 1

Figure 5:
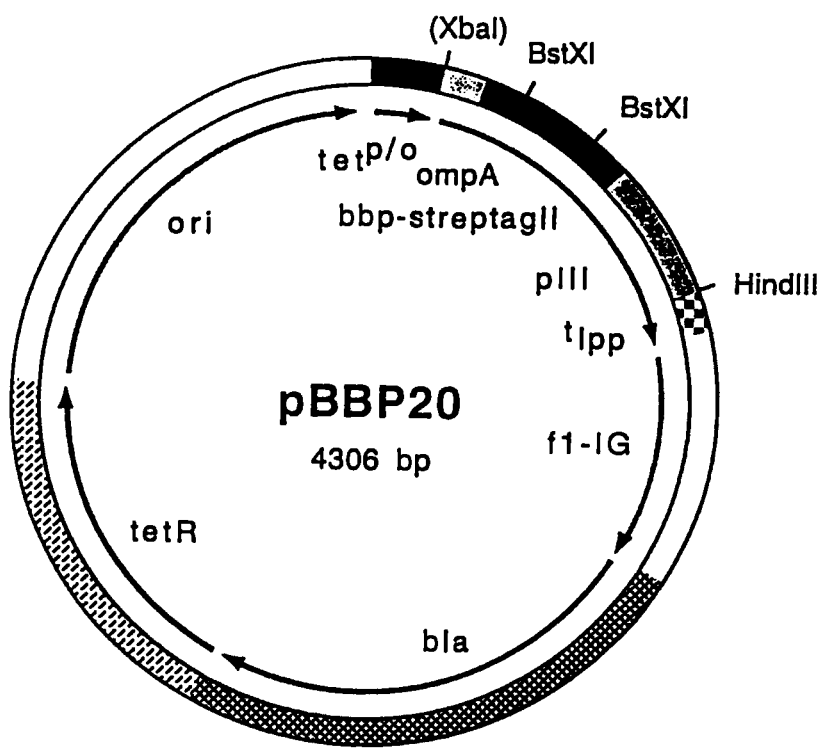
FIG. 5 schematically depicts the phasmid vector pBBP20.

Production of a Library for Lipocalin Muteins

Unless otherwise indicated, genetic engineering methods known to the person skilled in the art were used, as for example described in Sambrook et al. (Molecular Cloning. A Laboratory Manual (1989), Cold Spring Harbor Press).

PCR was applied in multiple steps according to FIG. 4 for the concerted mutagenesis of in total 16 selected amino acid positions in the four peptide loops of Bbp. The PCR reactions were carried out in a volume of 50 µl in both of the first amplification steps, wherein 10 ng pBBP20 plasmid DNA were employed as template as well as 25 pmol of the respective in primers, which had been synthesized according to the conventional phosphoramidite method. In addition, the reaction mixture contained 5 µl 10×Taq buffer (100 mM Tris/HCl pH 9.0, 500 mM KCl, 1% v/v Triton X-100), 3 µl 25 mM MgCl$_2$, 4 µl dNTP-Mix (2.5 mM dATP, dCTP, dGTP, dTTP). After bringing to volume with water, the mixture was overlayed with mineral oil and was heated to 94° C. for 2 minutes in an automated thermocycler. Subsequently 2.5 u Taq DNA-polymerase (5 u/µl, Promega) were added and 20 temperature cycles of 1 minute at 94° C., 1 minute at 60° C. and 1.5 minute at 72° C. were carried out, followed by an incubation for 5 minutes at 60° C. The desired amplification products were isolated from Low Melting Point Agarose (Gibco BRL) by preparative agarose gel electrophoresis using the Jetsorb DNA extraction kit (Genomed) according to the instructions of the manufacturer.

The subsequent amplification step was carried out in a 100 µl mixture, wherein approximately 6 ng of both of these respective fragments were used as templates, and 50 pmol of each of the primers SEQ ID NO:6 and SEQ ID NO:7 as well as 1 pmol of the oligodeoxynucleotide SEQ ID NO:5. The remaining components of the PCR mixture were added in the double amounts as in the previous amplification steps. PCR took place with 20 temperature cycles of 1 minute at 94° C., 1 minute at 55° C., 1.5 minutes at 72° C., followed by a subsequent incubation for 5 minutes at 60° C. The expected fragment was again isolated by preparative agarose gel electrophoresis.

For the cloning of this fragment representing the library of the lipocalin muteins in nucleic acid form, it was first cut with the restriction enzyme BstXI (New England Biolabs) according to the instructions of the manufacturer. The purification of the nucleic acid fragment obtained (335 base pairs, bp) again took place by means of preparative agarose gel electrophoresis. The DNA of the vector pBBP20 was analogously cut with BstXI and the larger of the two fragments (3971 bp) was isolated.

For the ligation, 0.93 µg (4.2 pmol) of the PCR fragment and 11 µg (4.2 pmol) of the vector fragment was incubated in the presence of 102 Weiss Units T4 DNA ligase (New England Biolabs) in a total volume of 500 µl (50 mM Tris/HCl pH 7.8, 10 mM MgCl$_2$, 10 mM DTT, 1 mM ATP, 50 µg/ml BSA) for two days at 16° C. The DNA was subsequently precipitated by adding 10 µg tRNA from yeast (Boehringer Mannheim), 25 µl 5 M ammonium acetate and 100 µl ethanol per 24 µl of ligation mixture. Incubation at −20° C. for three days was followed by centrifugation (25 minutes, 16000 g, 4° C.). Each precipitate was washed with 200 µl ethanol (70% v/v, −20° C.) and dried under vacuum. The DNA was finally dissolved in 43.6 µl TE/10 (1 mM Tris/HCl pH 8.0, 0.1 mM EDTA pH 8.0). The DNA concentration of the solution obtained was estimated by analytical agarose gel electrophoresis via the fluorescence intensity of the bands stained with ethidium bromide in comparison to a sample of known concentration.

The preparation of electrocompetent cells of the *E. coli* K12 strain XL1-blue (Bullock et al., supra) took place according to the methods described by Tung and Chow (Trends Genet. 11 (1995), 128-129) and by Hengen (Trends Biochem. Sci. 21 (1996), 75-76). 1 l LB-medium was adjusted by addition of a stationary XL1-blue overnight culture to an optical density at 600 nm of OD$_{600}$=0.08 and was incubated at 200 rpm and 26° C. in a 2 l Erlenmeyer flask. After reaching an OD$_{600}$=0.6, the culture was cooled for 30 minutes on ice and subsequently centrifuged for 15 minutes at 4000 g and 4° C. The cell sediment was washed twice each with 500 ml ice-cold 10% w/v glycerol and was finally resuspended in 2 ml of ice-cold GYT-medium (10% w/v glycerol, 0.125% w/v yeast extract, 0.25% w/v tryptone).

The Easyjec T basic system (EquiBio) was used with the accompanying cuvettes (electrode separation 2 mm) for the electroporation. All steps were carried out in the cold room at 4° C. Each 5 to 6 µl of the DNA solution mentioned above (245 ng µl) was mixed with 40 µl of the cell suspension, was incubated 1 minute on ice and was finally transferred to the cuvette. After the electroporation the suspension was immediately diluted in 2 ml of fresh, ice-cold SOC-medium (2% w/v tryptone, 0.5% w/v yeast extract, 10 mM NaCl, 10 mM MgSO$_4$, 10 mM MgCl$_2$) and was shaken for 60 minutes at 37° C. and 200 rpm. The cells were subsequently each sedimented for 2 minutes at 3600 g, were resuspended in 1 ml LB-medium with 100 µg/ml ampicillin (LB/Amp) and were plated at portions of 200 µl on agar plates (140 mm diameter) with LB/Amp-medium. Bei employing in total 10.7 µg of the ligated DNA, 3.73×10$^8$ transformants were obtained in this way with eight electroporation runs, and the transformants were distributed onto 40 agar plates and were further used according to Example 2.

Example 2

Phagemid Presentation and Selection of Anticalins Against Fluorescein

The cells plated onto LB/Amp-agar, which were transformed with the phasmid vectors coding for the library of the lipocalin muteins as fusion proteins, were incubated for 14 hours at 32° C. The colonies were then scraped from the agar plates with respective addition of 10 ml 2×YT/Amp-medium, were transferred to a sterile Erlenmeyer flask and were shaken for 20 minutes at 37° C., 200 rpm for complete suspension. 500 ml of 2×YT/Amp-medium prewarmed to 37° C. were inoculated with 2.3 ml of this suspension so that the cell density OD$_{550}$ was 0.08.

This culture was incubated at 37° C., 160 rpm to a cell density of OD$_{550}$=0.5, was infected (multiplicity of infection approximately 10) with VCS-M13 helper phage (Strategene) and was shaken for additional 30 minutes at 37° C., 160 rpm. Kanamycin (70 µg/ml) was subsequently added, the incubator temperature was lowered to 26° C. and, after 10 minutes, anhydrotetracycline was added to 25 µg/l (250 µl of a 50 µg/ml stock solution in dimethylformamide, DMF) to induce gene expression. Incubation continued for another 7 hours at 26° C., 160 rpm.

50 ml were removed from this culture and the cells were sedimented by centrifugation (15 minutes, 12000 g, 4° C.). The supernatant containing the phagemid particles was sterile-filtered (0.45 µm), was mixed with ¼ volumes (12.5 ml) 20% w/v PEG 8000, 15% w/v NaCl, and was incubated overnight at 4° C. After centrifugation (20 minutes, 18000 g, 4° C.) the precipitated phagemid particles were dissolved in 2 ml of cold PBS (4 mM KH$_2$PO$_4$, 16 mM Na$_2$HPO$_4$, 115 mM NaCl, pH 7.4). The solution was incubated on ice for 30 minutes and was distributed into two 1.5 ml reaction vessels. After centrifugation of undissolved components (5 minutes, 18500 g, 4° C.) each supernatant was transferred to a new reaction vessel.

Mixture with ¼ volumes 20% w/v PEG 8000, 15% w/v NaCl and incubation for 30 to 60 minutes on ice followed in order to reprecipitate the phagemid particles. After centrifugation (20 minutes, 18500 g, 4° C.) the supernatant was removed and the precipitated phagemid particles were dissolved in a total of 1 ml PBS. After incubation for 30 minutes on ice the solution was centrifuged (5 minutes, 18500 g, 4° C.) and the supernatant was used directly for the affinity enrichment.

Immuno-sticks (NUNC) were used for the affinity enrichment of the recombinant phagemids carrying the anticalin fusion proteins. These were coated overnight with 800 µl of a conjugate from bovine serum albumin (BSA) and 4-glutarylamido-fluorescein (100 µg/ml) in PBS.

For the production of the conjugate, 4-amino-fluorescein (fluoresceinamine isomer I, Fluka) was first reacted with a 15-fold molar excess of glutaric anhydride at pH 7.0 according to the procedure of Ogamo et al. (Carbohydrate Res. 105 (1982), 69-85), in order to later ensure the steric accessibility of the fluorescein group. The reaction product 4-glutarylamido-fluorescein, which carried a carboxylic acid group on an aliphatic side chain suitable for coupling with BSA, was subsequently purified by recrystallization from acetone/water. A solution of 17.3 mg (37.5 µmol) of this substance in 25 µl DMF was then mixed with 4.31 mg (37.5 µmol) N-hydroxysuccinimide in 25 µl DMF as well as with 7.2 mg (37.5 µmol) 1-ethyl-3-(3-dimethylaminopropyl)carbodiimide for activation. The mixture was incubated for 1 hour at room temperature (RT). 20 µl of this solution was mixed with a solution of 10 mg BSA in 980 µl 5% w/v NaHCO$_3$ pH 8.1 and incubated for 3 hours at RT. After removal of excess reactants from the BSA-conjugate by means of a PD-10 gel filtration column (Pharmacia), a coupling with 8 molecules of 4-glutarylamido-fluorescein per BSA-molecule was determined via absorption of the fluorescein group at 495 nm ($\epsilon$=72000 M$^{-1}$ cm$^{-1}$).

Unoccupied binding sites on the surface of the Immuno-Stick were saturated by incubation with 1.2 ml 2% w/v BSA in PBST (PBS with 0.1% v/v Tween 20) for 2 hours at RT. After washing quickly three times with 1.2 ml PBST each, the Immuno-Stick was incubated in a mixture of 250 µl of the phagemid solution and 500 µl of blocking buffer (2% w/v BSA in PBST) for 1 hour at RT.

For the removal of non-bound phagemids, washing followed eight times (in the first selection) or ten times (in selection cycles 2 to 6), each time with 950 µl PBST for 2 minutes. Adsorbed phagemids were finally eluted by 10 minute treatment of the Immuno-Stick with 950 µl 0.1 M glycine/HCl pH 2.2, wherein the pH of the elution fraction was subsequently immediately neutralized by mixing with 160 µl 0.5 M Tris.

For the amplification, this phagemid solution (1.1 ml, depending on the selection cycle between 10$^6$ and 10$^8$ Colony-forming Units) was shortly warmed to 37° C., was mixed with 4 ml of an exponentially growing culture of *E. coli* XL1-blue (OD$_{550}$=0.5), and was incubated for 30 minutes at 37° C., 200 rpm. The cells infected with the phagemids were subsequently sedimented (2 minutes, 4420 g, 4° C.), were resuspended in 800 µl of the culture medium, and were plated out onto four agar plates with LB/Amp-medium (140 mm diameter).

For the repeated production and affinity enrichment of phagemid particles the same procedure as described at the beginning of this example was used. In these cases 50 ml 2×YT/Amp-medium was inoculated with 0.2 to 1 ml of the suspension of the cells grown on the agar plates. Five further selection cycles with the BSA-fluorescein conjugate were carried out in this way.

Example 3

Production of the Anticalins

For the preparative production of the anticalins the gene cassette between both BstXI-cleavage sites from the pBBP20 vector was subcloned in the expression plasmid pBBP21. The Bbp originally encoded on pBBP21 was also produced as a control.

For the subcloning the phasmid DNA was isolated using the QIAprep Spin Miniprep Kit (QIAGEN) from the mixture of the *E. coli*-cells from Example 2, which were infected with the phagemids of the last selection cycle. This was cut with the restriction enzyme BstXI and the smaller of the two fragments (335 bp) was purified by preparative agarose gel electrophoresis as described in Example 1. The DNA of the vector pBBP21 was cut with BstXI in the same way and the larger of the two fragments (4132 bp) was isolated.

For the ligation 1.5 Weiss Units T4 DNA Ligase (Promega) were added to each 50 fmol of both DNA-fragments in a total volume of 20 μl (30 mM Tris/HCl pH 7.8, 10 mM MgCl$_2$, 10 mM DTT, 1 mM ATP) and this was incubated for 5 hours at 16° C. *E. coli* TG1-F$^-$ (*E. coli* K12 TG1, which had lost its episome through repeated culturing under non-selective conditions) was then transformed with 5 μl of this ligation mixture according to the CaCl$_2$-method (Sambrook et al., supra).

The plasmid-DNA was isolated from ten of the colonies obtained and the ligation was checked by restriction analysis with the enzymes HindIII and KpnI. All ten plasmids showed the expected fragment sizes of 342 and 4125 bp.

Sequence analysis of the Bbp-gene cassettes was performed by means of the T7 sequencing kit (Pharmacia) according to the instructions of the manufacturer using the oligodeoxynucleotides SEQ ID NO:8 and SEQ ID NO:9. In doing so, among the ten isolated plasmids, only four different sequences were found, the gene products of which were designated FluA, FluB, FluC and FluD. The DNA sequence of FluA was present twice, that of FluB four times, that of FluC three times, and that of FluD once. The nucleotide sequences of FluA, FluB, and FluC were translated into amino acid sequences and those amino acids deviating from Bbp are given in table 1.

The protein production of the corresponding clones was carried out on a 50 ml scale in order to study the binding activity of the anticalins in an ELISA (Example 4). To this end, 4 ml of LB/Amp-medium were inoculated with a single colony of the TG1-F$^-$ transformant carrying the respective plasmid, and was incubated overnight at 30° C., 200 rpm. 50 ml of LB/Amp-medium were then inoculated with 500 μl of this preculture and were shaken at 22° C., 200 rpm to an OD$_{550}$=0.5. Induction followed with 200 μg/l anhydrotetracycline (50 μl of a 200 μg/ml-stock solution in DMF) followed by shaking for 3 further hours at 22° C., 200 rpm. The cells were sedimented by centrifugation (15 minutes, 4420 g, 4° C.) and were resuspended in 1 ml cold periplasmic release buffer (100 mM Tris/HCl pH 8.0, 500 mM Saccharose, 1 mM EDTA). Incubation for 30 minutes on ice followed after addition of 25 μl of a solution of 1 mg/ml lysozyme to the periplasmic release buffer. The spheroplasts were sedimented by centrifugation (15 minutes, 18500 g, 4° C.) and the supernatant was transferred into a new reaction vessel as the periplasmatic protein extract.

For large scale protein production a 50 ml-preculture (LB/Amp-medium) was inoculated directly with a single colony of the TG1-F$^-$-strain transformed with the corresponding plasmid and was shaken at 30° C., 200 rpm overnight. In the case of the anticalins FluA and FluB, the *E. coli* strain JM83 (Yanisch-Perron et al., Gene 33 (1985), 103-119), which does not carry a supE gene, was used. The total preculture was used for inoculation of 2 l LB/Amp-medium in a 5 l-Erlenmeyer flask, after which the culture was incubated at 22° C., 200 rpm. Induction with 200 μg/l anhydrotetracycline (200 μl of a 2 mg/ml stock solution in DMF) was performed at a cell density of OD$_{550}$=0.5, followed by shaking for further 3 hours at 22° C., 200 rpm.

The cells were centrifuged (15 minutes, 4420 g, 4° C.) and, after decanting the supernatant, were resuspended in 20 ml of the periplasmic release buffer with cooling on ice. After addition of 50 μg/ml lysozyme (100 μl of a solution of 10 μg/ml lysozyme in the periplasmic release buffer) incubation followed for 30 minutes on ice. Subsequently the spheroplasts were separated in two subsequent centrifugation steps (15 minutes, 4420 g, 4° C. and 15 minutes, 30000 g, 4° C.). The periplasmatic protein extract isolated in this way was dialyzed against CP-buffer (100 mM Tris/HCl pH 8.0, 150 mM NaCl, 1 mM EDTA), was sterile-filtered, and was used for the chromatographic purification.

The purification took place by means of the Strep-Tag II-affinity tag (Schmidt et al., supra) fused to the C-terminus of the lipocalin mutein. In the present case the streptavidin mutein "1" was employed (German Patent Application 196 41 876.3; Voss and Skerra, Protein Eng. 10 (1997), 975-982), which was coupled to an activated sepharose (5 mg/ml immobilized streptavidin, relative to the bed volume of the matrix).

A 2 ml bed volume chromatography column filled with this material was equilibrated with 10 ml CP-buffer at 4° C. and a flow rate of 20 ml/h. Chromatography was monitored by measuring the absorption at 280 nm of the eluate in a flow-through photometer. After the application of the periplasmatic protein extract, the column was washed with CP-buffer until the base line was reached and the bound anticalin was subsequently eluted with 10 ml of the solution of 2.5 mM D-desthiobiotin (Sigma). The fractions containing the purified anticalin were checked via SDS-polyacrylamide gel electrophoresis (Fling and Gregerson, Anal. Biochem. 155 (1986), 83-88) and were pooled. The protein yields were between 200 μg and 3 mg per 2 l culture.

TABLE 1

Sequence characteristics of selected Anticalins

| Amino Acid-Position | Bbp | FluA | FluB | FluC | HepC1 | HepC4 |
|---|---|---|---|---|---|---|
| 34 | Asn | Ser | Gln | Ser | Lys | Gln[a] |
| 35 | Ser | Pro | His | Lys | Thr | Ala |
| 36 | Val | Asn | Trp | Asn | Lys | Pro |
| 37 | Glu | Gly | Asp | Gly | Gln[a] | Gly |
| 58 | Asn | Arg | Arg | Arg | Leu | Pro |
| 60 | His | Asp | Arg | Thr | His | Asn |
| 69 | Ile | Met | His | Gln[a] | Phe | Ala |
| 88 | Leu | Arg | Val | Arg | Val | Trp |
| 90 | Tyr | Val | Arg | Val | Ala | Gly |
| 93 | Val | Tyr | Arg | Lys | Phe | Leu |
| 95 | Lys | Arg | Arg | Arg | Ser | Ala |
| 97 | Asn | Thr | Gly | Gly | Gln | Trp |
| 114 | Tyr | Ser | Arg | Arg | Ala | Pro |
| 116 | Lys | Arg | Arg | Arg | Tyr | Arg |
| 125 | Gln | Trp | Trp | Leu | Val | Leu |
| 127 | Phe | His | His | His | Phe | Pro |
| 40[b] | Gly | | | Arg | Glu | |
| 68[b] | Phe | | | Val | | |
| 70[b] | Glu | | Lys | | | |
| 96[b] | Glu | Lys | | | | |
| 100[b] | Asn | | | | Ser | |

[a]These glutamic acid residues were encoded by amber stop codons.
[b]These amino acid substitutions arose due to random mutations.

Example 4

Measurement of the Affinity of the Anticalins for Fluorescein and its Derivatives For the detection of binding in an ELISA (Enzyme-linked Immunosorbent Assay) the wells of a microtiter plate (Micro Test III Flexible Assay Plate; Falcon) were first each filled with 100 μl of a 100 μg/ml solution of the BSA-fluorescein conjugate from Example 2 in PBS and were incubated overnight at RT. Unconjugated BSA served as a control. The solution was removed and unoccupied binding sites were saturated with 200 μl 2% w/v BSA in PBST for 2 hours. After washing three times with PBST, 100 µl of the periplasmatic protein extract from the production on the 50 ml scale (Example 3) were filled into the wells. Dilution series in PBST were prepared starting from this protein solution. 1 hour incubation at RT was followed again by rewashing three times with PBST, and a streptavidin-alkaline phosphate conjugate (Amersham), diluted 1:1000 with PBST, was filled into the wells. This enzyme conjugate served for the recognition of the Strep-Tag II-appendix at the C-terminus of the anticalins. Incubation was performed for 1 hour at RT and followed by washing two times with PBST and two times with PBS. Detection of the anticalins bound to the fluorescein groups finally took place via hydrolysis of p-nitrophenyl phosphate, catalyzed by the alkaline phosphatase. For this purpose, 100 µl of a solution of 0.5 mg/ml p-nitrophenyl phosphate (Amresco) in AP-buffer (100 mM NaCl, 5 mM $MgCl_2$, 100 mM Tris/HCl pH 8.8) were filled into the wells and the product formation was monitored by measuring the absorption at 405 nm in a SpectraMax 250 photometer (Molecular Devices).

In doing so, practically no binding was detected for FluD and Bbp, while FluA, FluB, and FluC showed intense binding signals. In comparison, the signal was strongest for FluC, followed by FluA and FluB.

The ligand-binding characteristics of the anticalins, were then determined by fluorescence titration. Here, the decrease in the intrinsic tyrosine and tryptophan fluorescence of the protein upon complex formation with the ligand was measured. The measurements were made with a fluorescence photometer (MS III, Photon Technology International Inc.) at an excitation wavelength of 280 nm (slit width 5 nm) and emission wavelength of 340 nm (slit width 10 nm). Fluorescein, 4-amino-fluorescein as well as its conjugate with glutaric acid from Example 2 were used as ligands. These three ligands showed no significant inherent fluorescence at the given wavelengths.

PBS with addition of 1 mM EDTA, pH 7.4 (adjusted with NaOH) served as buffer system. All solutions used were sterile-filtered (0.45 µm). The solution of the respective purified anticalin from Example 3 was dialyzed three times against this buffer and was adjusted to a concentration of 1 µM by dilution. The concentration was determined by absorption at 280 nm using calculated extinction coefficients of 63680 $M^{-1}$ $cm^{-1}$ for FluB as well as 52300 $M^{-1}$ $cm^{-1}$ for FluC. For FluA and Bbp, the corrected calculated extinction coefficients in the presence of guanidinium chloride according to Gill and von Hippel (Anal. Biochem. 182 (1989), 319-326) of 59755 $M^{-1}$ $cm^{-1}$ (FluA) as well as 54150 $M^{-1}$ $cm^{-1}$ (Bbp) were used.

For the measurement, 2 ml of the anticalin solution was applied in a quartz cuvette equipped with a stirring bar and thermostatted at 25° C. in the sample holder of the photometer. Subsequently altogether 40 µl of a 250 µM to 1 mM solution of the ligand in the same buffer were added by pipetting in steps of 1 µl to 4 µl. The accompanying dilution of the applied protein solution of maximally 2 was not taken into account in the subsequent analysis of the data. After every titration step the sample was incubated for 1 minute with stirring for equilibration, and the fluorescence signal was measured as an average value over 10 s. After subtraction of the fluorescence value for the buffer, the signals were normalized to a starting value of 100% and were corrected for the inner filter effect of the ligand. For this purpose, fluorescence titrations were carried out with the respective ligand, in which the anticalin solution was replaced by N-Acetyl-L-tryptophanamide (Sigma).

The measured values of a titration series obtained in this way were fitted to the following equation by non-linear regression with the help of the computer program Kaleidagraph (Abelbeck Software):

$$F = ([P]_t - [L]_t - K_d)\frac{f_P}{2} + ([P]_t + [L]_t + K_d)\frac{f_{PL}}{2} + (f_P - f_{PL})\sqrt{\frac{([P]_t + [L]_t + K_d)^2}{4} - [P]_t[L]_t}$$

Here, F is the normalized fluorescence intensity and $[P]_t$ the concentration of the anticalin. $[L]_t$ is the total concentration of the ligand in each titration step. $f_{PL}$ and $K_d$ were fitted as free parameters to the data measured and represent the fluorescence coefficients of the anticalin-ligand complex as well as the thermodynamic dissociation constants of this complex, respectively. In the case of FluC, $[P]_t$ was additionally fitted as a free parameter. The dissociation constants determined for the anticalins FluA, FluB, and FluC are given in table 2. The binding effect in the measurement for comparison with Bbp was so weak that a dissociation constant could not be determined in this case.

TABLE 2

Dissociation constants for the complexes of anticalins and fluorescein derivatives

|  | Fluorescein | 4-Aminofluorescein | 4-Glutarylamidofluorescein |
|---|---|---|---|
| FluA | 118 ± 14 nM | 224 ± 6 nM | 601 ± 16 nM |
| FluB | 5.73 ± 0.86 µM | 2.84 ± 0.3 µM | 4.70 ± 0.51 µM |
| FluC | 411 ± 20 nM | 299 ± 41 nM | 78 ± 3 nM |

Example 5

Selection of Anticalins Against a Hepatitis C-Peptide Epitope

For the selection of the anticalins, the library made in Example 1 was used. The amplification and isolation of the phagemids took place exactly as described in Example 2. A biotinylated synthetic hepatitis C-peptide epitope corresponding to the peptide fragment no. 59 from the surface protein NS4 of HCV (Khudyakow et al., Virology 206 (1995), 666-672) was used as peptide ligand. The peptide, SEQ ID NO:13, was synthesized according to the common Fmoc-method using a PS3 automat (RAININ Instrument Co.), wherein Rink amide MBHA-resin (Novabiochem) was used. Subsequent to the coupling of the amino acid building blocks from the C- to the N-terminus, amino caproic acid was coupled as a boc-protected derivative and, in the last step, D-biotin (Sigma) was coupled. The peptide, cleaved from the resin and deprotected, was purified by HPLC and its composition was checked by ESI-mass spectrometry.

For the affinity enrichment of the recombinant phagemids carrying the anticalin fusion proteins, superparamagnetic particles coated with streptavidin (Dynabeads M-280 streptavidin, Dynal) were used. The amount of the peptide ligand was adjusted such that it was on the one hand present in molar excess relative to the phagemids employed, and that on the other hand the binding capacity of the streptavidin for the biotin groups was not exceeded.

For this purpose, 20 μl of the peptide solution (20 μg/ml in PBS) was mixed with 280 μl of a solution of freshly prepared phagemid (3.0×10$^{12}$ cfu/ml) and was incubated for 1 hour at RT, after which 100 μl of a solution of 8% w/v BSA, 0.4% v/v Tween 20 in PBS was added. Parallel to this 100 μl of the commercially available suspension of the magnetic particles were washed three times each with 100 μl PBS and were incubated with 100 μl 2% w/v BSA in PBST for 1 hour at RT in order to saturate unspecific binding sites. After removal of the supernatant, the peptide/phagemid mixture was added to the magnetic particles, they were resuspended and incubated for 10 minutes at RT. To saturate free biotin binding sites of the streptavidin, 10 μl of a solution of 4 μM desthiobiotin in PBS were finally added to the mixture and it was incubated for 5 minutes at RT.

For the removal of unbound phagemids, the magnetic particles were washed 8 times with 1 ml each of PBST, 0.1 μm desthiobiotin. To this end the magnetic particles were collected at the wall of 1.5 ml. Eppendorf tube with the help of a magnet and the supernatant was decanted. Following this, the magnetic particles were resuspended with fresh buffer and were held in suspension for 1 minute by rotation of the vessel. The elution of the bound phagemids took place by a 10 minute incubation of the resuspended particles in 950 μl 0.1 M glycin/HCl pH 2.2. The pH value of the solution was subsequently immediately neutralized by addition of 160 μl 0.5 M Tris.

Subsequently the eluted phagemids were propagated as described in Example 2 and were implemented for a new affinity selection under the conditions given above. In total, 6 selection cycles were carried out.

Example 6

Identification of Peptide-Binding Anticalins by Use of the "Colony Screening"-Method For the analytical production of the anticalins as fusion proteins with the Strep-Tag II as well as with the albumin-binding domain and their characterization by "colony screening", the gene cassette between both BstXI cleavage sites from the vector pBBP20 was subcloned into pBBP22.

For this purpose the phasmid DNA was isolated from the mixture of the *E. coli* clones obtained by infection with the phagemids from Example 5 eluted during the last selection cycle, using the QIAprep Spin Miniprep Kits (QIAGEN). The DNA was cut with the restriction enzyme BstXI and the smaller of the two fragments (335 bp) was purified by preparative agarose-gel electrophoresis as described in Example 1. The DNA of the vector pBBP22 was cut with BstXI and the larger of the two fragments (3545 bp) was isolated in the same way.

For the ligation, each 50 fmol of the two DNA-fragments were mixed with 1.5 Weiss Units T4 DNA ligase (Promega) in a total volume of 20 μl (30 mM tris/HCl pH 7.8, 10 mM MgCl$_2$, 10 mM DTT, 1 mM ATP) and this was incubated overnight at 16° C. *E. coli* TG1-F$^-$ was transformed with 5 μl of this ligation mixture according to the CaCl$_2$-method.

A hydrophilic PVDF membrane (Millipore, type GVWP, pore size 0.22 μm), labelled at one position and cut to size, was laid onto an LB/Amp agar plate and 150 μl of the cell suspension from the transformation batch were uniformly plated out onto this membrane. The amount of transformation batch plated out was measured such that approximately 500 colonies were obtained. The plate was incubated for 6.5 hours at 37° C. in the incubation cabinet until the colonies had reached a size easily recognizable by the naked eye.

In the meantime a hydrophobic membrane (Millipore, Immobilon P, pore size 0.45 μm), also cut to size, was moistened with PBS according to the instructions of the manufacturer. It was subsequently agitated for 4 hours at RT in a solution of 10 mg/ma human serum albumin (HSA, Sigma) in PBS. Remaining binding sites on the membrane were saturated by incubation with 3% w/v BSA, 0.5% v/v Tween 20 in PBS for 2 hours at RT. The membrane was washed twice for 10 minutes each with 20 ml PBS and agitated afterwards for 10 minutes in 10 ml LB/Amp medium, to which 200 μg/l anhydrotetracycline were added. It was subsequently marked at one position and was laid onto a culture plate with LB/Amp agar, which additionally contained 200 μg/l anhydrotetracycline. The hydrophilic membrane on which the colonies were grown was laid onto the hydrophobic membrane in such a way that both of the marks superimposed. The culture plate was incubated with both membranes at 22° C. for 15 hours. During this phase the respective lipocalin muteins from the colonies were secreted and were immobilized via the albumin-binding domain on the HSA on the lower membrane.

After this, the upper membrane with the colonies was transferred to a fresh LB/Amp agar plate and stored at 4° C. The hydrophilic membrane was removed, was washed three times for 10 minutes each with 20 ml PBST, and was subsequently incubated 1 hour in 10 ml of a solution of 1 μM SEQ ID NO:13 in PBST. After washing twice in PEST, incubation followed for 1 hour with 10 ml avidin-alkaline phosphatase conjugate (ExtrAvidin-AP-Conjugate, Sigma, dilution 1:1000 in PBST). The membrane was subsequently washed for 5 minutes each twice with PBST and twice with PBS and agitated for 10 minutes in AP-buffer (0.1 M Tris/HCl pH 8.8, 0.1 M NaCl, 5 mM MgCl$_2$). For the chromogenic detection reaction, the membrane was incubated in 10 ml AP-buffer, to which 30 μl BCIP (50 μg/ml in dimethylformamide) and 5 μl NBT (75 μg/ml in 70% v/v dimethylformamide) were added, until distinct color signals could be recognized at the positions of some of the colonies. In this way the binding activity for the peptide ligand of the anticalins produced by these colonies was detected.

Eight of these colonies were cultured. The plasmid DNA was isolated and the Bbp gene cassette was subjected to sequence analysis as in Example 3. All clones exhibited different sequences. The characteristic amino acids of the anticalins HepC1 and HepC4 are given in table 1.

Example 7

Use of the Anticalins for the Detection of Hepatitis C Peptide Epitopes in a Sandwich-ELISA Starting from the clones found in Example 6, the corresponding anticalins were produced as fusion proteins with the Strep-Tag II and the albumin-binding domain. Gene expression took place on a 50 ml scale. To this end 4 ml each of LB/Amp medium were inoculated with a single colony of TG1-F$^-$ carrying the respective plasmid and were incubated overnight at 30° C., 200 rpm. 500 μl of each pre-culture were then used for inoculation of 50 ml LB/Amp medium and were shaken at 22° C., 200 rpm to an OD$_{550}$=0.5. After that induction was performed with 200 μg/l anhydrotetracycline (50 μl of a 200 μg/ml stock solution in DMF), followed by shaking for 3 further hours at 22° C., 200 rpm. The cells were sedimented by centrifugation (15 minutes, 4420 g, 4° C.) and were re-suspended in 1 ml each of cold periplasmic release buffer (100 mM Tris/HCl pH 8.0, 500 mM saccharose, 1 mM EDTA). After addition of 25 μl of a solution of 1 mg/ml lysozyme to the periplasmic release buffer, incubation followed for 30 minutes on ice. The spheroplasts were sedimented by centrifugation (15 minutes, 18500 g, 4° C.) and the supernatant was transferred to a new reaction vessel as the periplasmatic protein extract.

For the ELISA, the wells in a microtiter plate (ELISA-STRIP, 2×8 wells, KO, F-form, high binding capacity, Greiner) were each filled with 200 µl of a solution of 20 mg/ml HSA in 50 mM NaHCO$_3$ pH 9.6 and were incubated for 1 hour at RT. After removal of the solution, the unoccupied binding sites were saturated with 200 µl 3% w/v BSA in PBS with 0.5% v/v Tween 20 for 1 hour. After washing three times with PBST, 50 µl of the undiluted periplasmic protein extract were filled into the respective first well of a row. 50 µl PBS were first placed into each of the subsequent wells of each row. 50 µl of the periplasmic protein extract were then pipetted into the respective second well, were mixed, and, starting from this, 1:2 dilutions in the subsequent wells were prepared in a stepwise manner. The periplasmic protein extract with the Bbp, which was made using pBBP22 as expression plasmid, served as a control.

After 1 hour incubation at RT washing followed three times with PBST, followed by pipetting of 200 µl of the ligand solution (SEQ ID NO:13, 1 µM in PBST) into each well. After 1 hour incubation at RT, washing followed with PBST and, after that, 50 ml avidin-alkaline phosphatase conjugate (ExtrAvidin-AP-Conjugate, Sigma), diluted 1:1000 in PBST, were added to each well. Incubation followed for 1 hour at RT, with subsequent washing twice with PBST and twice with PBS. The detection of the bound anticalin took place by means of a chromogenic reaction in the presence of p-nitrophenylphosphate. To this end, 100 µl of a solution of 0.5 mg/ma p-nitrophenylphosphate (Amresco) in AP-buffer were placed in each well and product formation was measured by absorption at 405 nm in a SpectraMax 250 photometer (Molecular Devices) as dA/dt number.

Figure 7:
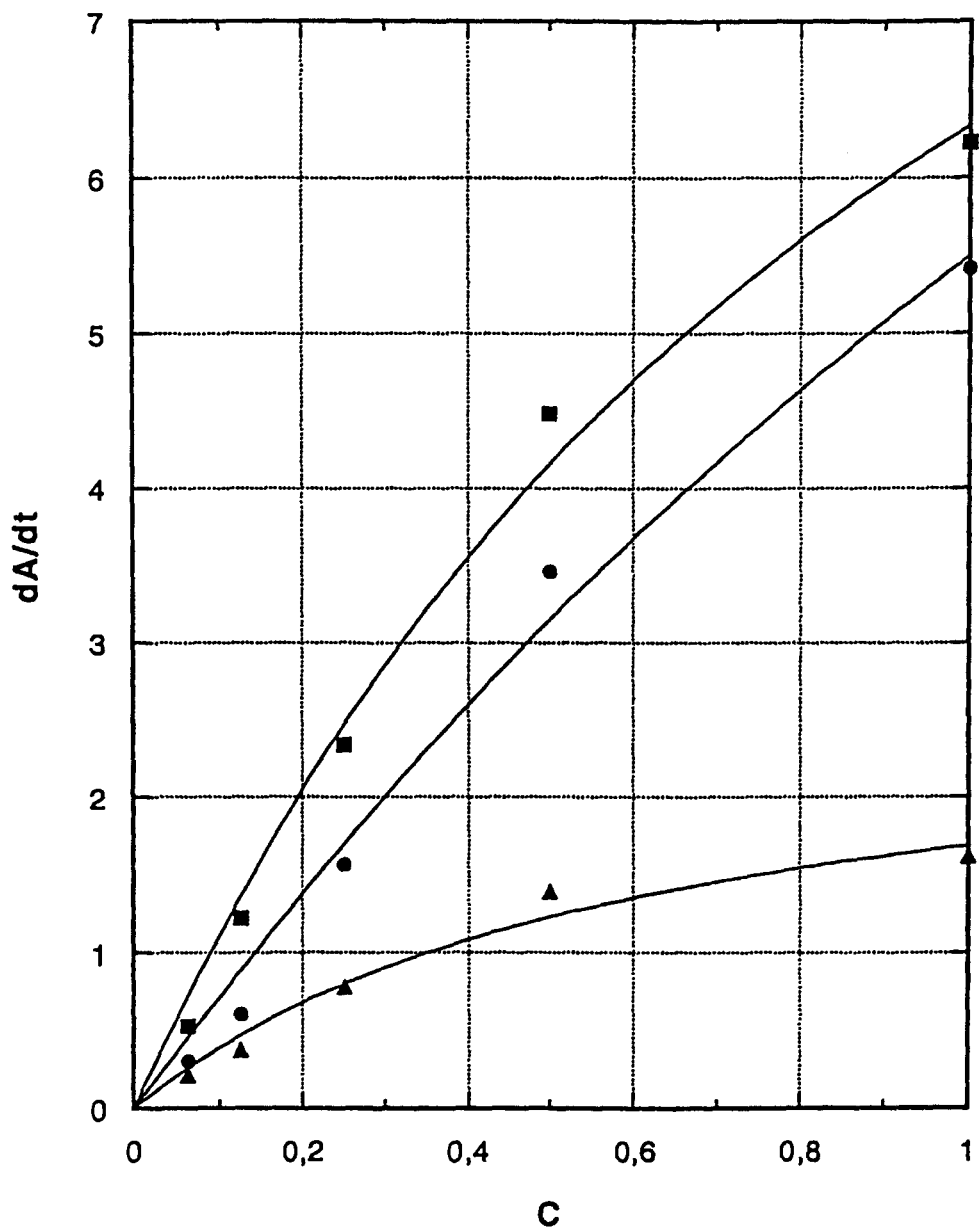
FIG. 7 demonstrates the binding of a peptide by anticalins in) an ELISA.

In the case of Bbp, only low signals were detectable, whereas all anticalins analyzed showed clear binding. The signal for HepC1 was strongest, followed by HepC4. The binding curves for HepC1, HepC4 and Bbp are represented in FIG. 7.

Example 8

Use of the Anticalin FluA to Quench the Inherent Fluorescence of Fluorescein

Complex formation was followed by fluorescence titration of a solution of fluorescein with different concentrations of the anticalin FluA. Here, the decrease in the intensity of the intrinsic fluorescence of the fluorescein ligand was measured. The measurements were made with a LS 50 B fluorescence photometer (Perkin Elmer) at an excitation wavelength of 490 nm (slit width 4 nm) and an emission wavelength of 512 nm (slit width 4 nm).

PBS supplemented with 1 mM EDTA of pH 7.4 (adjusted with NaOH) served as the buffer system. All solutions used were sterile-filtered (0.45 µm). The solution of the purified anticalin FluA from the Example 3 was dialyzed three times against this buffer. The concentration was determined using an extinction coefficient of 59755 $M^{-1}$ $cm^{-1}$ for FluA.

For a measurement series, a set of 15 solutions with a constant fluorescein concentration of 1 µM and varying respective protein concentrations from 0 to 10 µM was made, each in a total volume of 120 µl. For this purpose, each 6 µl of a 20 µM solution of fluorescein in the mentioned buffer were mixed with different volumes of the anticalin stock solution and brought to a total volume of 120 µl with buffer.

For the measurement of the fluorescence intensity as depending on the respective concentration of the anticalin, the individual solutions were transferred to a quartz microcuvette and thermostatted in the sample holder of the photometer for 1 minute at 25° C. The fluorescence signal was subsequently measured as an average value over 10 seconds. After subtraction of the fluorescence value for the buffer, the signals were scaled to an initial value of 100%. A further correction of the measured values proved to be unnecessary.

It appeared that the initially high fluorescence intensity of the fluorescein decreased significantly with increasing concentration of the anticalin until only a very small fluorescence could be measured. The measured values obtained for the titration series were fitted according to the following formula by non-linear regression with the help of the computer program Kaleidagraph (Abelbeck Software):

$$F = ([L]_t - [P]_t - K_d)\frac{f_L}{2} + ([P]_t + [L]_t + K_d)\frac{f_{PL}}{2} + (f_L - f_{PL})\sqrt{\frac{([P]_t + [L]_t + K_d)^2}{4} - [P]_t[L]_t}$$

Here, F is the scaled fluorescence intensity and $[L]_t$ the concentration of fluorescein (1 µM). $[P]_t$ represents the total concentration of FluA in the respective titration step. $f_{PL}$ and $K_d$ were fitted to the measured data as free parameters and they denote the fluorescence coefficient of the complex of the anticalin FluA with fluorescein as well as their thermodynamic dissociation constants.

Figure 8:
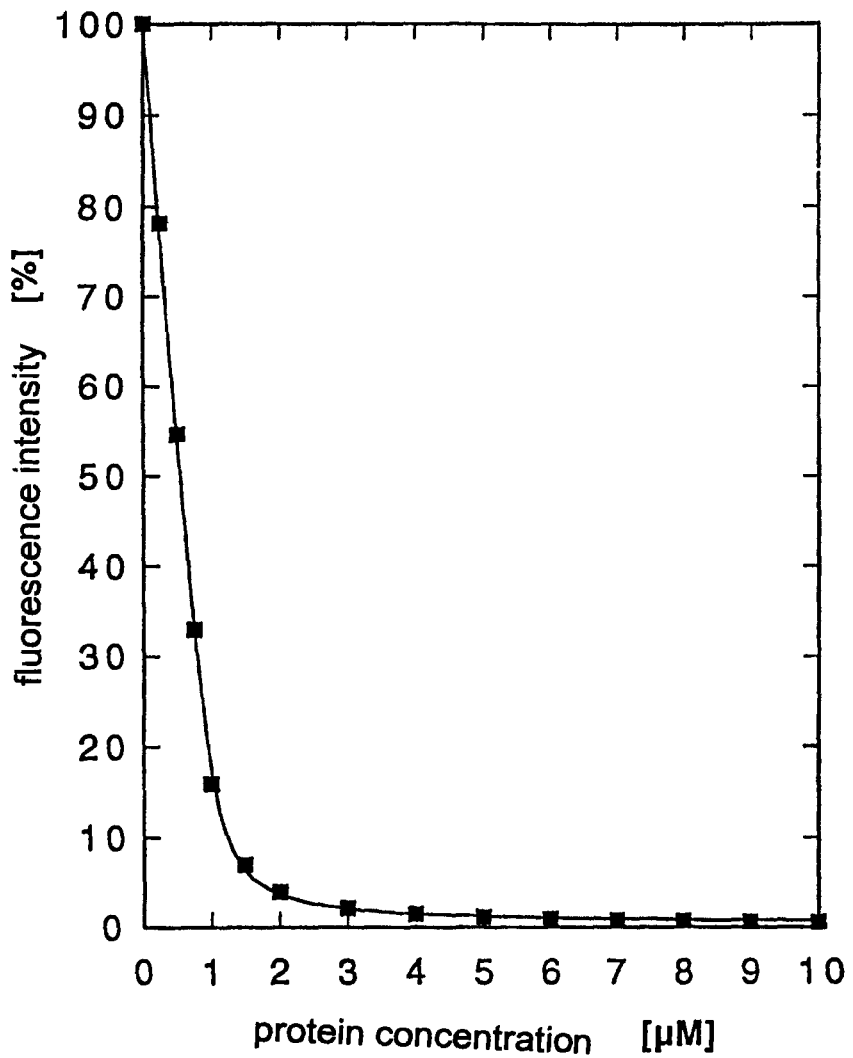
FIG. 8 depicts the complexation and fluorescence quenching of the ligand fluorescein by an anticalin in a fluorescence titration.

The measured fluorescence intensity values measured and the fitted curves are represented in FIG. 8. A value of 35.2±3.2 nM was determined as the dissociation constant for the complex of the anticalin FluA and fluorescein. In the formation of the complex with the anticalin FluA, the fluorescence intensity of fluorescein was quenched by 99.7±0.3%, i.e. it was almost quantitatively quenched. In the corresponding control experiment with the recombinant BBP, no comparable fluorescence quenching was found.

The invention claimed is:

1. An isolated lipocalin mutein having a cylindrical β-pleated sheet supersecondary structural region comprising eight β-strands connected pair-wise by four peptide loops at one end to define thereby a binding pocket, said four peptide loops structurally corresponding to those segments which comprise amino acids 28-45, 58-69, 86-99, and 114-129 of the linear polypeptide sequence of the bilin binding protein of *Pieris brassicae* SEQ ID NO: 20, wherein at least one amino acid of each of at least three of said four peptide loops has been mutated and wherein said lipocalin mutein is effective to bind a ligand with a determinable affinity of at least $10^5$ $M^{-1}$.

2. The lipocalin mutein of claim 1, wherein the lipocalin mutein is derived from a human lipocalin.

3. The lipocalin mutein of claim 2, wherein the lipocalin mutein is derived from human apolipoprotein D and the mutated amino acids in the region of the four peptide loops correspond to sequence positions 34-37, 59, 61, 70, 87, 89, 92, 94, 96, 113, 115, 123 and 125 of the linear polypeptide sequence of human apolipoprotein D as set forth in SEQ ID NO: 19.

4. The lipocalin mutein of claim 2, wherein the lipocalin mutein is derived from human retinol-binding protein and the mutated amino acids in the region of the four peptide loops correspond to sequence positions 32-35, 57, 59, 73, 90, 92, 95, 100, 102, 119, 121, 131, and 133 of the linear polypeptide sequence of human retinol binding protein as set forth in SEQ ID NO: 18.

5. The lipocalin mutein of claim 1, wherein at least one amino acid of each of said four peptide loops has been mutated.

6. The lipocalin mutein of claim 1, wherein the lipocalin mutein is bound to a solid phase, and wherein the bound lipocalin mutein binds a ligand.

7. The lipocalin mutein of claim 1, wherein the lipocalin mutein is fused to a fusion partner.

8. The lipocalin mutein of claim 7, wherein the fusion partner is selected from the group consisting of the albumin-binding domain of protein G, protein A, an antibody fragment, an oligomerizing domain, a toxin and a lipocalin mutein with different or the same ligand specificity.

9. The lipocalin mutein of claim 1, wherein the lipocalin mutein is coupled to a further compound.

10. The lipocalin mutein of claim 9, wherein the further compound is selected from the group consisting of a protein, a radioactive moiety and a molecule with a defined binding characteristic.

11. The lipocalin mutein of claim 10, wherein the protein is selected from the group consisting of an enzyme, an antibody, and a lipocalin mutein with different or the same ligand specificity.

* * * * *